US012708400B2

(12) United States Patent
Penrod et al.

(10) Patent No.: US 12,708,400 B2
(45) Date of Patent: Aug. 18, 2026

(54) DEVICES AND METHODS FOR REMOVAL OF MATERIAL IN A VASCULATURE

(71) Applicant: VERGE MEDICAL, INC., Campbell, CA (US)

(72) Inventors: Jonathan James Penrod, Kalamazoo, MI (US); Mehrdad Farhangnia, San Francisco, CA (US); Thomas Davis, West Bloomfield, MI (US); Theodore Karmon, Suttons Bay, MI (US); Brian Carter Wolfe, Kalamazoo, MI (US)

(73) Assignee: Verge Medical, Inc., Campbell, CA (US)

( * ) Notice: Subject to any disclaimer, the term of this patent is extended or adjusted under 35 U.S.C. 154(b) by 180 days.

(21) Appl. No.: 18/377,701

(22) Filed: Oct. 6, 2023

(65) Prior Publication Data

US 2024/0260988 A1 Aug. 8, 2024

Related U.S. Application Data

(63) Continuation-in-part of application No. 18/129,715, filed on Mar. 31, 2023, now Pat. No. 12,588,926, (Continued)

(51) Int. Cl.
*A61B 17/3207* (2006.01)

(52) U.S. Cl.
CPC .......................... *A61B 17/320758* (2013.01); *A61B 2217/005* (2013.01)

(58) Field of Classification Search
CPC ........ A61B 17/3207; A61B 17/320758; A61B 2217/005
See application file for complete search history.

(56) References Cited

U.S. PATENT DOCUMENTS

| | | | |
|---|---|---|---|
| 4,378,708 | A | 4/1983 | Pouliot |
| 4,858,478 | A | 8/1989 | Kush et al. |

(Continued)

FOREIGN PATENT DOCUMENTS

| | | | |
|---|---|---|---|
| WO | 2009100210 | A1 | 8/2009 |
| WO | 2015168179 | A1 | 11/2015 |

(Continued)

OTHER PUBLICATIONS

International Search Report and Written Opinion mailed Apr. 27, 2021, in corresponding International Application No. PCT/US2021/016886 (9 pages).

(Continued)

*Primary Examiner* — Ashley L Fishback
(74) *Attorney, Agent, or Firm* — Michele V. Frank; Venable LLP

(57) ABSTRACT

A device for removing material from a vasculature includes a rotation subassembly having a first central axis and a first gear, a valve subassembly having the first central axis and being adjacent to the rotation subassembly, and an actuation system having a second central axis and a second gear. The rotation subassembly is coupled to a catheter to rotate the catheter. The valve subassembly is configured to selectively allow flow of the material from the catheter to the device. The actuation system configured to actuate rotation of the rotation subassembly. The first central axis and the second central axis are parallel.

16 Claims, 33 Drawing Sheets

Related U.S. Application Data which is a continuation of application No. 17/856,846, filed on Jul. 1, 2022, now Pat. No. 11,648,029, which is a continuation of application No. 17/535,361, filed on Nov. 24, 2021, now Pat. No. 11,376,035, which is a continuation of application No. PCT/US2021/016886, filed on Feb. 5, 2021.

(60) Provisional application No. 63/378,801, filed on Oct. 7, 2022, provisional application No. 63/036,091, filed on Jun. 8, 2020, provisional application No. 62/971,424, filed on Feb. 7, 2020.

(56) References Cited

U.S. PATENT DOCUMENTS

| | | | |
|---|---|---|---|
| 5,007,896 | A | 4/1991 | Shiber |
| 5,030,201 | A | 7/1991 | Palestrant |
| 6,824,551 | B2 | 11/2004 | Trerotola |
| 6,929,633 | B2 | 8/2005 | Evans et al. |
| 7,041,084 | B2 | 5/2006 | Fojtik |
| 7,235,088 | B2 | 6/2007 | Pintor et al. |
| 7,367,982 | B2 | 5/2008 | Nash et al. |
| 7,534,234 | B2 | 5/2009 | Fojtik |
| 7,655,016 | B2 | 2/2010 | Demarais et al. |
| 7,674,247 | B2 | 3/2010 | Fojtik |
| 7,887,560 | B2 | 2/2011 | Kusleika |
| 7,976,511 | B2 | 7/2011 | Fojtik |
| 7,988,677 | B2 | 8/2011 | Fojtik |
| 8,337,450 | B2 | 12/2012 | Fojtik |
| 8,491,539 | B2 | 7/2013 | Fojtik |
| 8,539,644 | B2 | 9/2013 | Fojtik |
| 8,628,549 | B2 | 1/2014 | To et al. |
| 8,672,893 | B2 | 3/2014 | Fojtik |
| 8,672,900 | B2 | 3/2014 | Fojtik |
| 8,845,621 | B2 | 9/2014 | Fojtik |
| 8,920,402 | B2 | 12/2014 | Nash et al. |
| 8,992,482 | B2 | 3/2015 | Fojtik |
| 9,022,971 | B2 | 5/2015 | Fojtik |
| 9,107,691 | B2 | 8/2015 | Fojtik |
| 10,058,656 | B2 | 8/2018 | Fumiyama et al. |
| 10,179,224 | B2 | 1/2019 | Yang et al. |
| 10,207,057 | B2 | 2/2019 | Fojtik |
| 10,307,242 | B2 | 6/2019 | Walzman |
| 10,352,411 | B2 | 7/2019 | Fojtik |
| 10,405,924 | B2 | 9/2019 | Bowe |
| 11,002,346 | B2 | 5/2021 | Fojtik |
| 11,071,827 | B2 | 7/2021 | Fumiyama et al. |
| 11,191,931 | B2 | 12/2021 | Fojtik |
| 2004/0122345 | A1 | 6/2004 | Muller |
| 2007/0250096 | A1 | 10/2007 | Yamane et al. |
| 2007/0255252 | A1 | 11/2007 | Mehta |
| 2008/0098564 | A1 | 5/2008 | Fojtik |
| 2009/0088702 | A1 | 4/2009 | Fojtik |
| 2010/0152611 | A1 | 6/2010 | Parihar et al. |
| 2010/0217122 | A1 | 8/2010 | Fumiyama et al. |
| 2011/0009888 | A1 | 1/2011 | Shturman |
| 2012/0095447 | A1 | 4/2012 | Fojtik |
| 2013/0103046 | A1 | 4/2013 | Shiber |
| 2013/0345644 | A1 | 12/2013 | Fojtik |
| 2014/0005634 | A1 | 1/2014 | Fojtik |
| 2014/0142594 | A1 | 5/2014 | Fojtik |
| 2015/0032081 | A1 | 1/2015 | Fojtik |
| 2015/0231371 | A1 | 8/2015 | Rollins et al. |
| 2015/0359595 | A1 | 12/2015 | Ben Oren et al. |
| 2016/0270803 | A1 | 9/2016 | Masubuchi |
| 2017/0181760 | A1 | 6/2017 | Look et al. |
| 2017/0238949 | A1 | 8/2017 | Imai et al. |
| 2019/0105074 | A1 | 4/2019 | Kónya |
| 2019/0192175 | A1 | 6/2019 | Chida et al. |
| 2020/0367933 | A1 | 11/2020 | Laurito |
| 2020/0405338 | A1 | 12/2020 | Begg et al. |
| 2021/0236159 | A1 | 8/2021 | Fojtik |
| 2021/0332872 | A1 | 10/2021 | Fojtik |

FOREIGN PATENT DOCUMENTS

| | | | |
|---|---|---|---|
| WO | 2016164606 | A1 | 10/2016 |
| WO | 2018067518 | A1 | 4/2018 |
| WO | 2018145116 | A1 | 8/2018 |
| WO | 2018145124 | A1 | 8/2018 |

OTHER PUBLICATIONS

Jalal, Shwan et al., “Distal Cuff Occlusion: A Novel, Simple Approach for Distal Embolic Protection in Peripheral Vascular Intervention,” Sep. 2017, pp. 297-300, vol. 29, No. 9, The Journal of Invasive Cardiology (4 pages).

“ASPIRE Mechanical Thrombectomy System,” Medical Innovation. (Aug. 13, 2014). located at <https://youtu.be/j9p9F2nuCys>.

Non-Final Rejection dated Jul. 28, 2025, directed to U.S. Appl. No. 18/129,715; 12 pages.

60
118
40
26
114
24
100

200c
218c
214c 200b
218b
226b
214b 200a
218a
214a 60
418
419
436
400
414
424

500a

500b

500c

500d

500e

500f

DEVICES AND METHODS FOR REMOVAL OF MATERIAL IN A VASCULATURE

CROSS-REFERENCE TO RELATED APPLICATIONS

This application claims priority to U.S. Provisional Patent Application No. 63/378,801, filed Oct. 7, 2022. This application is a continuation-in-part application of U.S. patent application Ser. No. 18/129,715, filed Mar. 31, 2023, which is a continuation application of U.S. patent application Ser. No. 17/856,846, filed Jul. 1, 2022, now U.S. Pat. No. 11,648,029, which is a continuation application of U.S. patent application Ser. No. 17/535,361, filed Nov. 24, 2021, now U.S. Pat. No. 11,376,035, which is a continuation application of International Application No. PCT/US/2021/016886, filed Feb. 5, 2021, which claims priority to U.S. Provisional Patent Application No. 62/971,424, filed Feb. 7, 2020, and U.S. Provisional Patent Application No. 63/036,091, filed Jun. 8, 2020. The contents of each of the aforementioned applications are each hereby incorporated by reference in their entireties.

TECHNICAL FIELD

The present disclosure relates generally to devices and methods for removal of material in a vasculature. More particularly, the present disclosure relates to devices and methods combining suction through a catheter and rotation of a catheter to remove material in a vasculature.

BACKGROUND

Endoscopic interventions may be performed in the lower extremity due to blockages in the vasculature such as chronic total occlusions, long lesions, and focal lesions. These interventions often occur in the femoral popliteal or infra popliteal vasculature. Physicians will treat these conditions using percutaneous transluminal angioplasty (PTA), stenting, and/or atherectomy devices. Often times the thrombus, clot, and distal emboli involved in these interventional procedures needs to be removed. A need exists for removal of material from a vasculature.

BRIEF SUMMARY

According to an embodiment, a device for removing material from a vasculature, having a rotation subassembly having a first central axis and a first gear, the rotation subassembly coupled to a catheter to rotate the catheter, a valve subassembly having the first central axis and being adjacent to the rotation subassembly, the valve subassembly configured to selectively allow flow of the material from the catheter to the device, and an actuation system having a second central axis and a second gear, the actuation system configured to actuate rotation of the rotation subassembly, wherein the first central axis and the second central axis are parallel.

According to an embodiment, the device includes the catheter.

According to an embodiment, the rotation subassembly comprises a body, the first gear, and a coupling configured to connect to the catheter.

According to an embodiment, wherein the body, the first gear, and the coupling are monolithic and unitary.

According to an embodiment, further comprising a protrusion extending within the coupling and forming an annular space with the body, wherein an end of the catheter is configured to be received within the annular space.

According to an embodiment, comprising an internal threaded surface in the annular space, the internal threaded surface configured to correspond to a threaded surface on the end of the catheter.

According to an embodiment, the first gear includes gear teeth and a protrusion having two lobes and the actuation system includes a helix having two protrusions, wherein the two protrusions are received within the two lobes to allow co-rotation between the helix and the first gear.

According to an embodiment, the actuation system further comprising a trigger, a free shuttle, and a drive shuttle.

According to an embodiment, wherein the free shuttle includes two protrusions configured to be received within respective openings of the trigger.

According to an embodiment, wherein the free shuttle and the drive shuttle are configured to move longitudinally along the second central axis.

According to an embodiment, wherein the drive shuttle is configured to rotate only in one direction about the second central axis.

According to an embodiment, wherein the free shuttle has a first ratchet profile and the drive shuttle has a second ratchet profile, the first ratchet profile configured to mate with the second ratchet profile.

According to an embodiment, wherein the mating of the first ratchet profile and the second ratchet profile allows rotation of the drive shuttle in a first direction and prevents rotation of the drive shuttle in a second direction.

According to an embodiment, wherein the first ratchet profile and the second ratchet profile each comprise a plurality of steps.

According to an embodiment, further comprising a helix.

According to an embodiment, wherein the helix has an external helix profile and the drive shuttle has an internal helix profile, wherein the internal helix profile is configured to mate with the external helix profile to allow relative rotation between the helix and the drive shuttle.

BRIEF DESCRIPTION OF DRAWINGS

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION

The present disclosure relates to devices and methods of suctioning material through a catheter and rotating the catheter to assist in removal of the material. In an example method, the device is used in conjunction with an external cuff placed distal to the location of an interventional procedure to be performed and/or distal to the location of the device in the vasculature. The cuff occludes the vasculature. The distal end of the catheter is placed in the vasculature near the dam caused by the external cuff. Using rotation of the catheter and suction through the catheter, material is removed from the vasculature through the device. The material may be debris caused by an interventional procedure and/or may be other material (e.g., blood clot, occlusion) located in the vasculature. In example devices, actuation systems are provided that convert the linear motion caused by pulling a handle trigger to a rotational motion of the distal tip of the catheter. Such linear motion conversion may be achieved with gears, cams, and/or cables. The device may allow for controlled suction through the catheter.

Figure 1:
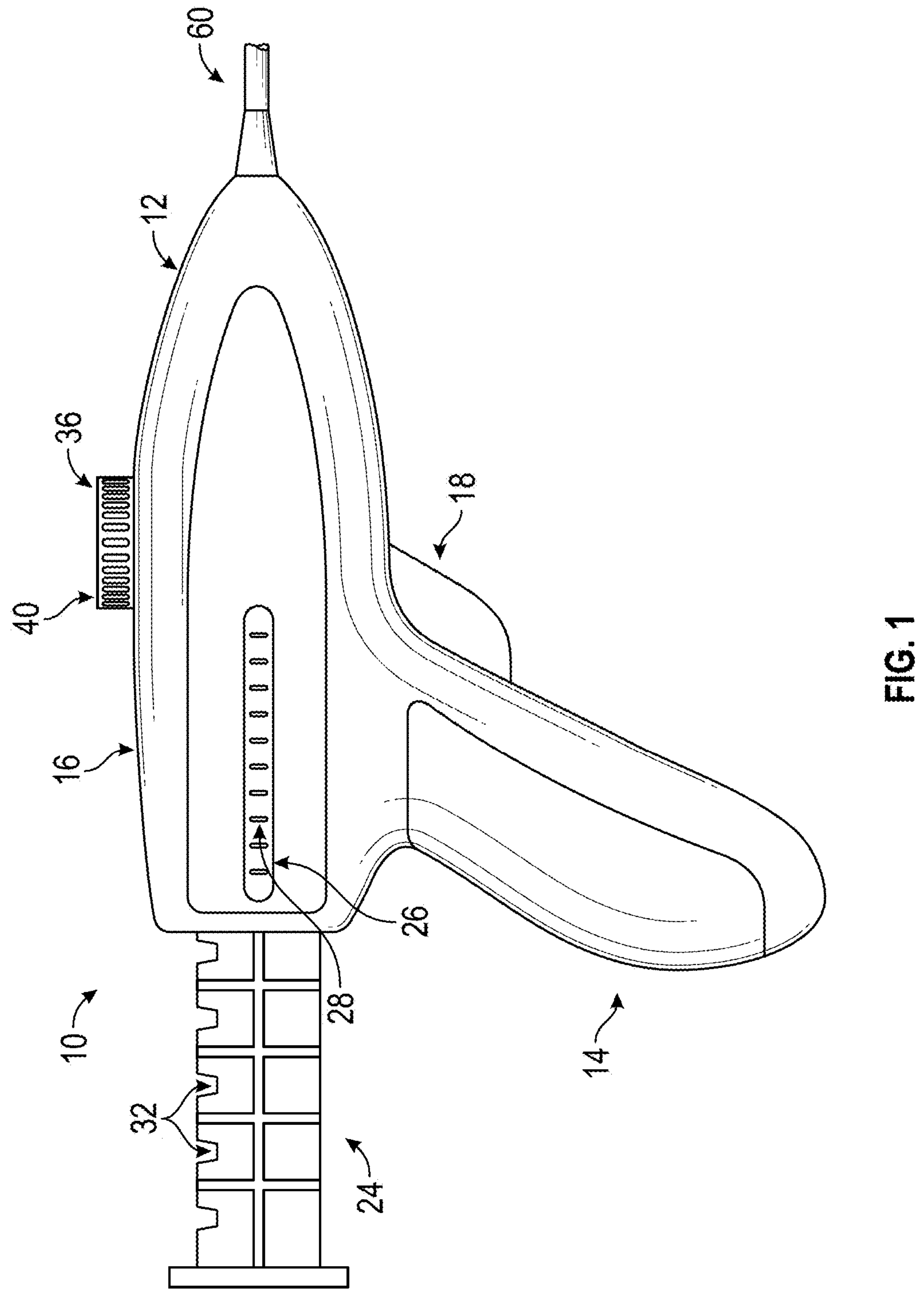
FIG. 1 shows an exemplary device, according to an embodiment of the present disclosure.
Figure 2:
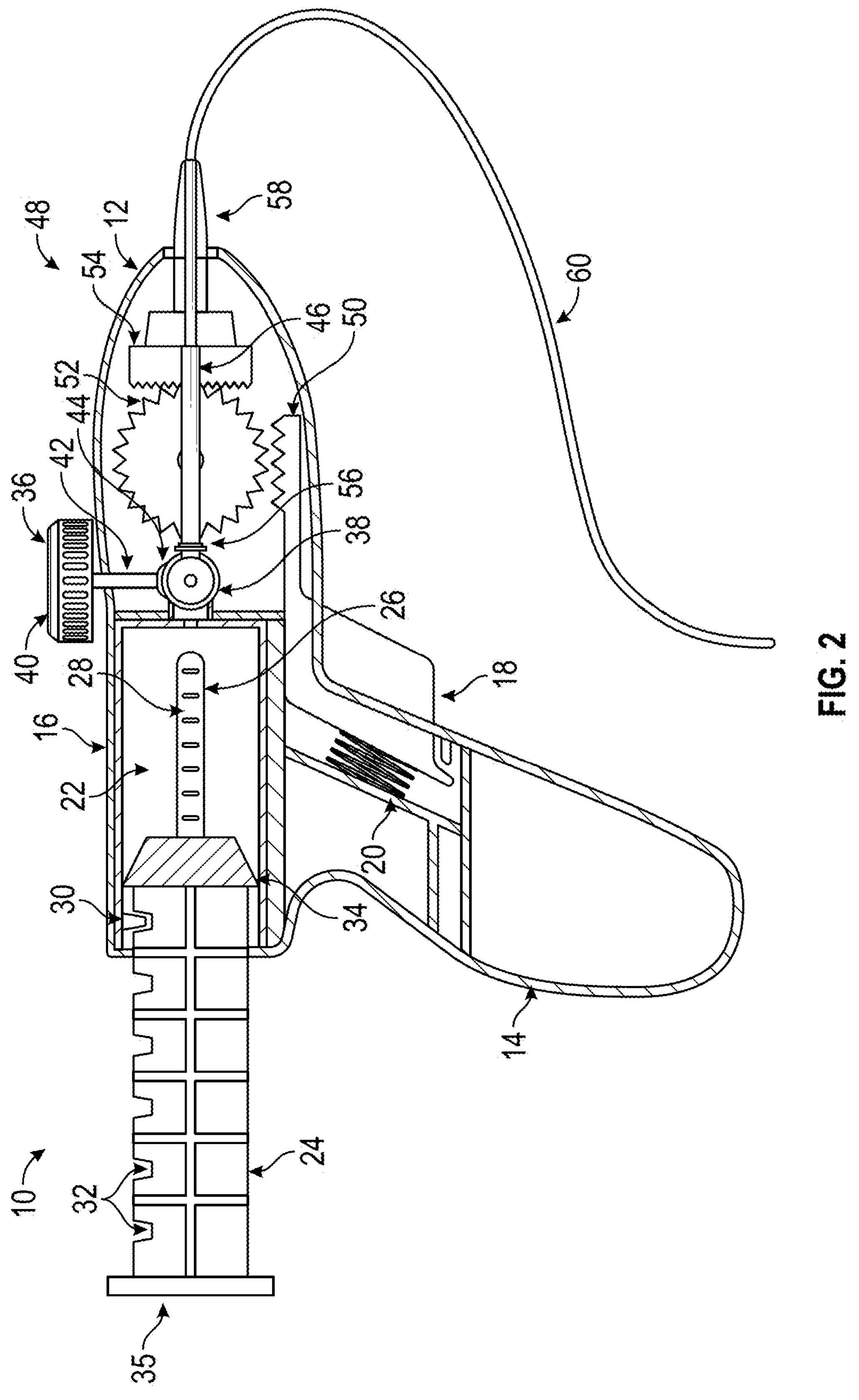
FIG. 2 shows a cross-sectional view of the exemplary device of FIG. 1, according to an embodiment of the present disclosure.

Referring to FIGS. 1 and 2, an exemplary device 10 is shown. Device 10 has a configuration to allow for suction and spinning of a catheter 60 and generally includes a handle 14 with a trigger 18, a plunger 24, and an actuation system 48. The device 10 may include a lateral portion 12 and the handle 14. The lateral portion 12 and handle 14 may have a housing 16. The housing 16 may be a unitary housing or may comprise more than one housing portion coupled together. The lateral portion 12 and the handle 14 may be formed together as a single, unitary component or may be formed as separate components coupled together.

The catheter 60 may be a hollow, cylindrical catheter having a lumen. The catheter 60 may be sized in both diameter and length based on the particular vasculature being treated, the procedure being performed, or both. The catheter 60 may have a proximal end coupled to the actuation system 48 with a coupling 58. The catheter 60 may have a distal end. The distal end may be placed proximate the location to be treated in the vasculature during use of the device 10. The distal end may include an opening into the lumen of the catheter 60. In some examples, the distal end of the catheter 60 may be equipped with a distal tip structure, such as shown and described in FIGS. 11A-11F.

The catheter 60 and/or device 10 may be further configured to contact the vasculature to loosen, scrape or otherwise contact impediments that exist in a targeted area. In an example, the catheter 60 may include a surface feature on the outer surface of the catheter. The surface feature may provide an abrasive outer surface to the catheter 60. The surface feature may be, for example, but not limited to, a coating, profile, protrusions, texture, roughened surface, etc. The catheter 60 may have a pipe cleaner type of outer characteristic. The catheter 60 may have a roughened outer surface. The outer surface of the catheter 60 may act as an agent that would lightly scrape the walls of the vasculature to loosen any impediments or loose impediments on the wall of the vasculature as the catheter 60 is rotated and/or translated longitudinally through the vasculature. Other parts of the device 10 may also be configured to accomplish this functionality.

The handle 14 may include the trigger 18 and a biasing member 20 (FIG. 2). The trigger 18 may be biased outward with respect to the handle 14 by the biasing member 20. Alternatively, the trigger 18 may be biased inward. The trigger 18 may be biased to a rest or inactive position. The biasing member 20 may be a spring, such as a coil spring, although other biasing devices are contemplated. The biasing member 20 may begin in a neutral state to be compressed by the trigger 18 during actuation of the device 10. When force is released from the trigger 18, the compressed biasing member 20 may extend back to the neutral state.

Referring to FIG. 2, the lateral portion 12 may include a chamber 22 and the plunger 24. The chamber 22 may be a hollow chamber, such as, for example, a hollow, cylindrical chamber. Other shapes of the chamber 22 are contemplated. The chamber 22 may include a window 26. The window 26 may allow for viewing, measuring, and/or monitoring of material to be collected in the chamber 22. The window 26 may be located on a side surface of the device 10, however alternative locations, such as, for example, the top or alternate side of the device 10 are consider. In an embodiment, the window 26 may extend around several sides of the device in a semi-cylindrical or cylindrical manner. The window 26 may include marks 28. The chamber 22 may include a lock 30 extending from an inner wall of the chamber 22. The lock 30 may extend downward from an inner, upper surface of the chamber 22, although other locations are contemplated. Although depicted as a triangular cross-section or generally trapezoidal or frustoconical shape, the lock 30 may have any shape. The shape of the lock 30 may mate, conform, or correspond to the shape of one or more notches 32 on the plunger 24. Although depicted and described as a lock and notch arrangement, other devices or arrangements that prevent relative movement of the plunger 24 with respect to the chamber 22 may be contemplated.

The plunger 24 may be cylindrical, although other shapes of the plunger 24 are contemplated. The plunger 24 may have a perimeter or shape that corresponds, conforms, or mates with an internal surface or shape of the chamber 22. For example, the chamber 22 may be a hollow cylinder and the plunger 24 may be a cylinder. In this manner, the plunger 24 may be adapted to move with respect to the chamber 22. The plunger 24 may include one or more notches 32. The one or more notches 32 may be located on the plunger 24 such that the one or more notches 32 may be selectively aligned with the lock 30. For example, where the lock 30 extends downward from an inner, upper surface of the chamber 22, the one or more notches 32 may extend downward form an outer, upper surface of the plunger 24. The one or more notches 32 may be openings, grooves, slots, indentations, or other shapes formed within the body of the plunger 24. The one or more notches 32 may be a single notch or groove that extends along the surface of the plunger 24. The one or more notches 32 may be a helical groove. The one or more notches 32 may be spaced along the plunger 24 to correspond to a volume or degree of vacuum allowed in the chamber 22. The plunger 24 may include a forward end 34 and a rear end 35. The forward end 34 may have an outer diameter that seals with an inner diameter of the chamber 22. The rear end 35 may allow for a user to push or pull or otherwise move the plunger 24 with respect to the chamber 22.

The lateral portion 12 may include a valve 36 and a valve 38. The valve 36 may be a manual stop valve. A user may rotate a knob 40 of the valve 36 to open and/or close the valve 36. The valve 36 may be opened and closed in an incremental fashion such that there exists partially opened or partially closed positions of the valve 36. Each turn of the knob 40 may open or close the valve 36 a predetermined degree. The valve 36 may be a ball valve. For example, the knob 40 may rotate a shaft 42 that rotates a ball 44. The ball 44 may have an opening therethrough. Rotation of the knob 40 may align, partially align, and/or misalign the opening of the ball 44 with a lumen, such as, for example, the lumen 46. The valve 38 may be a one-way valve. The valve 38 may permit fluid to flow from the lumen 46 into the chamber 22 but prohibit or prevent fluid from flowing from the chamber 22 to the lumen 46.

The lateral portion 12 may include the actuation system 48. The actuation system 48 may allow the trigger 18 to actuate a corresponding effect in a catheter, as will be described in more detail to follow. The actuation system 48 may include a rack 50, a pinion gear 52, and a crown gear 54. An interface 56, such as, for example, a rotational seal, may be located along the lumen 46 between the actuation system 48 and the valve 36. The interface 56 may allow the actuation system 48 to rotate without also rotating the valves 36 and 38. The interface 56 may prevent the chamber 22, plunger 24, valve 36, valve 38, and trigger 18 from rotating with the pinion gear 52, crown gear 54, and catheter 60. The rack 50 may be operably coupled to the trigger 18. The rack 50 may be integral or unitarily formed with the trigger 18. A coupling 58 may couple the actuation system 48 to a catheter 60. Thus, the actuation system 48 may impart a function, such as, for example, a rotational movement, on the catheter 60. The lumen 46 may extend from the catheter 60, through the coupling 58, crown gear 54, pinion gear 52, interface 56, valve 36, and valve 38. In this manner, material (e.g., fluid, debris, solid particles, etc.) may be transmitted from a lumen of the catheter 60 into the chamber 22 via the lumen 46.

The rack 50, pinion gear 52, and crown gear 54 may be selected based on the desired degree of rotation based on each depression of the trigger 18. The crown gear 54 may be a reduction gear. The crown gear 54 may be sized to achieve a desired number of rotations of the catheter 60 per actuation of the trigger 18. The smaller the crown gear 54, the more rotations of the catheter 60 may be achieved per actuation of the trigger 18. The coupling 58 may be a standard luer lock for coupling the catheter 60 to the device 10.

Figure 3A:
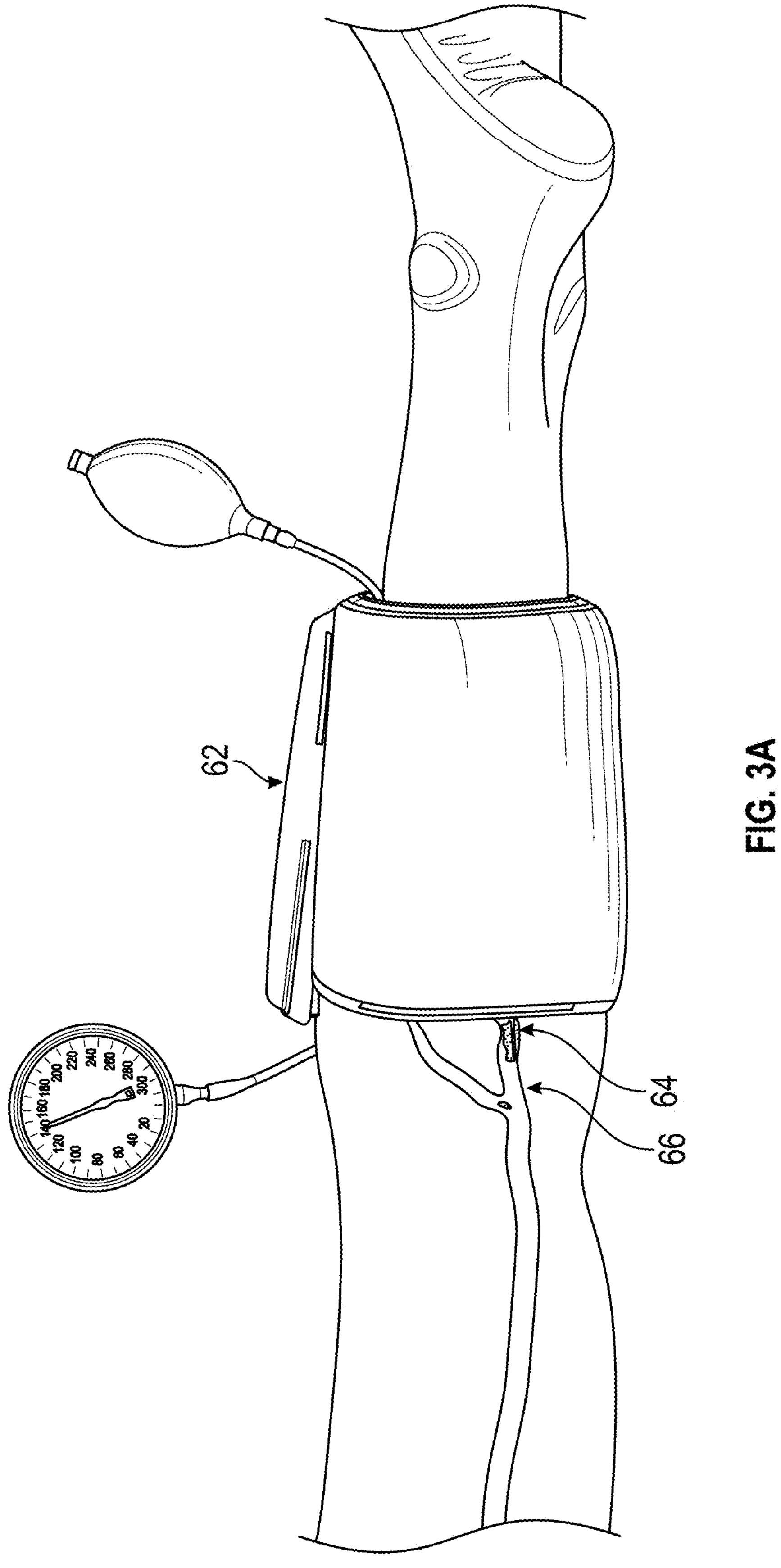
FIGS. 3A-3C show an exemplary method employing a device, according to an embodiment of the present disclosure.
Figure 3B:
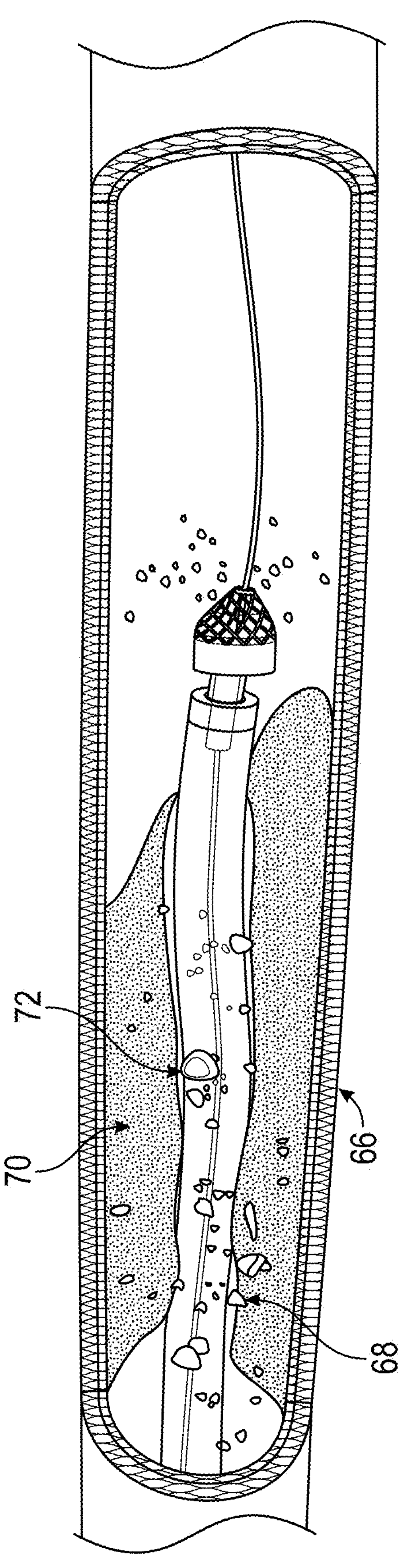
Figure 3C:
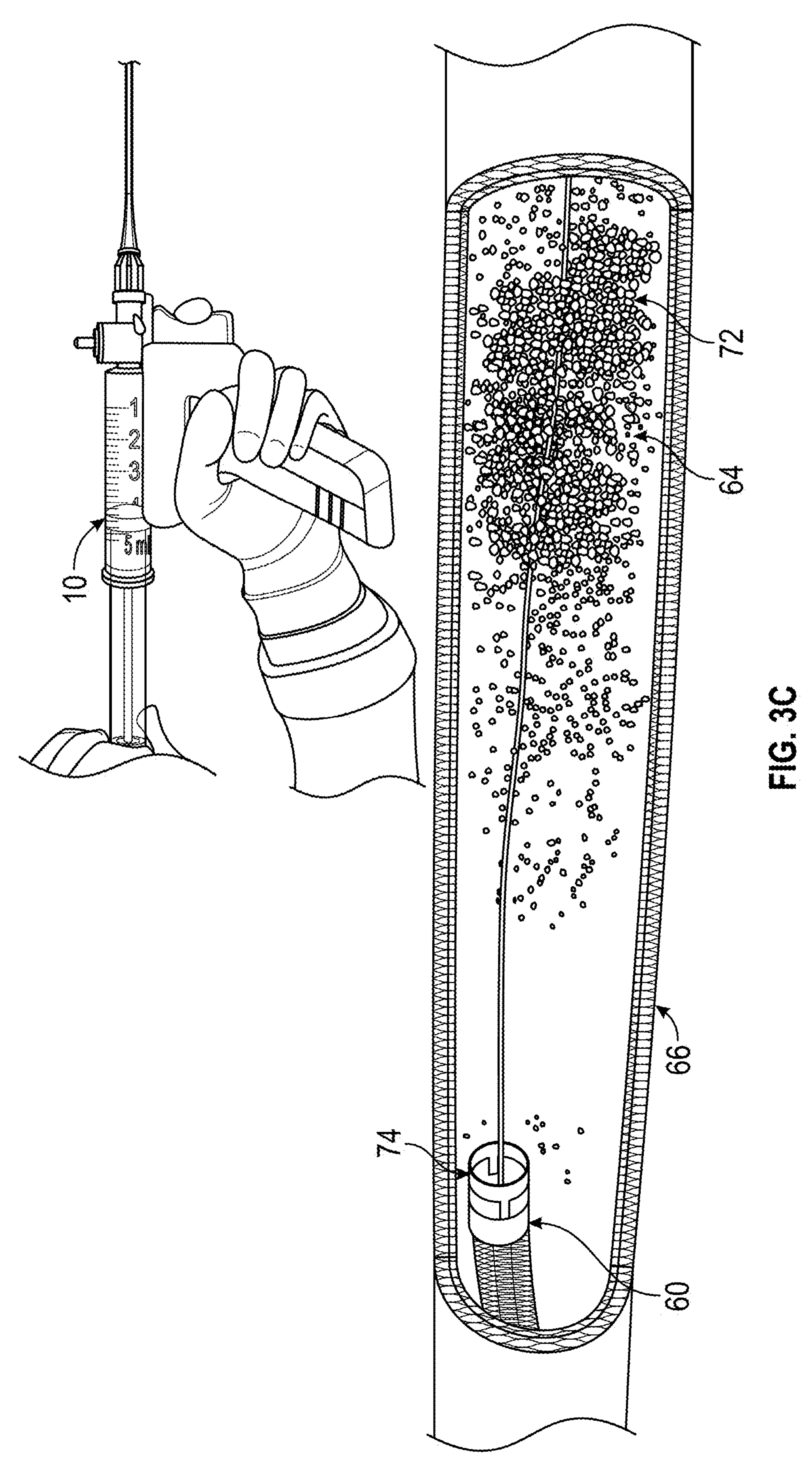

In operation, an interventional procedure may be performed within a vasculature of patient, such as, for example, an artery of a lower extremity of the patient as depicted in FIGS. 3A-3C. Other uses are contemplated, including, for example, arms or any appendage. For example, the user may remove, destroy or otherwise break-up a blockage or obstruction in the vasculature during a previously or concurrently performed interventional procedure. For example, the interventional procedure may include, but is not limited to, thrombectomy, atherectomy, stenting, balloon angioplasty, and other processes to recannulate a vessel. Although described in conjunction with an interventional device, in an exemplary use, the device may be used alone, not in conjunction with a separate interventional procedure/device. That is, for example, the device may perform the interventional procedure. For example, the device may remove material, such as, for example, but not limited, to a clot, within the vasculature.

Referring to FIGS. 3A-3C, an external cuff 62 may be placed distal to the location 64 of the material to be removed (e.g., distal to the location of an interventional procedure and/or distal to the location within the vasculature where the device is employed). The external cuff 62 may create a dam, blockage, or occlusion within the vasculature 66 such that material disturbed during use of the device (and/or during the interventional procedure, if applicable) may not flow in the vasculature 66 past the location of the external cuff 62. The external cuff 62 may be a cuff placed around the external surface of the patient. In the example where the device is employed in a lower extremity of the patient, the external cuff may be placed around the external surface of the lower extremity distal to the location where the distal end of the catheter of the device is placed and/or distal of the interventional procedure (e.g., around the outside of the leg as shown in FIG. 3A).

The external cuff 62 may operate as a tourniquet or cuff to restrict flow within the vasculature 66. The external cuff 62 may restrict flow in the vasculature 66 distal to the location of the cuff 62. The restriction of flow due to the cuff 62 may create a dam within the vasculature 66. The external cuff 62 may allow for monitoring and/or adjustment during the procedure (e.g., during use of the device of the present disclosure). The external cuff 62 may allow for adjustment of the pressure and/or flow within the vasculature. That is, after placement of the external cuff 62 on the patient, a medical professional may monitor the blood pressure within the vasculature being treated and adjust the pressure applied by the cuff 62 as necessary throughout the duration of the procedure (and/or use of the device 10). This may allow for the medical professional to control the restriction of flow distal to the cuff 62. If pressure within the vasculature increases, for example, the medical professional may adjust the cuff 62 accordingly to ensure the restriction of flow distal to the cuff is maintained.

The interventional procedure may occur prior to use of the device 10 or concurrently therewith. The interventional procedure may occur prior to insertion of the catheter 60, after insertion of the catheter 60, or concurrently therewith. In some examples, no interventional procedure may be performed and the device 10 may be employed to perform the interventional procedure with no other devices or systems. For example, in FIG. 3B, the interventional procedure may be performed after installation of the cuff 62, but before use of the device 10. In the case of FIG. 3B, the interventional procedure may be an atherectomy. Although, as discussed, other procedures are contemplated and the device 10 may be used alone, not in conjunction with an interventional procedure/device. In FIG. 3B, the interventional procedure may use an interventional device 68 that breaks up or disturbs an obstruction 70. Such a break up or destruction of the obstruction 70 may cause debris 72.

In use of the device 10 (or any of the devices described herein), a user may insert the catheter 60 in the vasculature 66 of the patient, as shown in FIG. 3C. A distal end 74 of the catheter 60 may be located near the location 64 of and upstream of the dam created by the external cuff (This may also be a location near the location of an interventional procedure, if applicable). The device 10 may suction or vacuum material (e.g., debris 72) from the location 64 of the distal end 74 of the catheter 60 through the distal end 74 of the catheter 60, up through a lumen of the catheter 60, and into the chamber 22 of the device 10. If an interventional procedure is also performed, the suctioning may occur simultaneously with the interventional procedure, after completion of the interventional procedure, or a combination thereof. The catheter 60 may rotate before, after, or simultaneously with the suctioning of material. Rotation of the catheter 60 may create turbulent flow which may facilitate entry of the material and fluid (e.g., blood) into the lumen of the catheter 60. Rotation of the catheter 60 may create a vortex at the distal top of the catheter 60 to upend the material. Rotation of the catheter 60 may agitate material, prevent or prohibit material from settling in any one location with the vasculature, and/or suspend the material within the fluid in the vasculature. This may enhance or promote the removal of material from the vasculature.

Referring to FIGS. 1, 2, and 3C, during use, the device 10 begins with the valve 36 in a closed position. The user inserts the catheter 60 into the vasculature being treated. Once at the desired location within the vasculature (e.g., a location near or within the dam created by the external cuff), the user may move the plunger 24 rearward (e.g., to the left in FIG. 2) with respect to a front end of the device 10. The user may rotate the plunger 24 such that a notch 32 aligned with the lock 30 is moved out of alignment. The user may then slide or pull the plunger 24 rearward. The lock 30 may not interfere with the outer surface of the plunger 24 during movement. When the desired position of the plunger 24 is achieved, the user may rotate the plunger 24 such that one of the notches 32 is in alignment with the lock 30. This may prevent the plunger 24 from moving with respect to the chamber 22 during use of the device 10. The lock 30, when engaged, may prevent the vacuum within the chamber 22 from pulling the plunger 24 into the chamber 22.

The user may select the appropriate notch 32 to align with the lock 30 based on the desired vacuum, based on a desired amount of material to be collected in the chamber 22, or a combination thereof. Each notch 32 may align with a predetermined vacuum force or chamber volume, or both, that the user may select from. For example, if the user desires a small amount of material to be collected or small vacuum force, the user may select a notch 32 closer to the rear end 35 such that the chamber 22 is reduced as compared to the total available volume of the chamber 22. If the user desires a large amount of material to be collected or large vacuum force, the user may select a notch 32 closer to the forward end 34 such that the chamber 22 is enlarged to the total volume or closer to the total available volume. Selecting the desired volume and vacuum of the chamber 22 may allow for the device to perform a controlled suction at the distal end of the catheter 60 within the vasculature.

Once the plunger 24 is in the desired location and locked in place, the user may turn the knob 40 to open the valve 36. Since the plunger 24 is moved with the valve 36 in a closed position a vacuum or negative pressure is created within the chamber 22. The plunger 24 and the valve 36 may form a negative pressure element. When the valve 36 is opened, material or fluid may be pulled by the negative pressure or vacuum in the chamber 22. That is, fluid and material in the vasculature at the distal end of the catheter 60 may flow through the lumen of the catheter 60, through the lumen 46 of the device 10, and into the chamber 22. A user may watch the amount of fluid and/or material collecting in the chamber 22 through the view window 26. The graduated marks 28 may allow the user to monitor and record the amount of material and/or fluid collected. The valve 38 may prevent any of the collected materials from traveling back out of the chamber 22, through the lumen 46 and back into the vasculature of the patient.

The suction effect of the device 10 may be operated independently of the rotation of the catheter 60 of the device 10 and vice versa. A user may elect to operate the suction before, after, or concurrently with rotation of the catheter 60. To rotate the catheter 60, the user may depress the trigger 18 against the force of the biasing member 20. As the trigger 18 is operatively coupled to the rack 50, depression of the trigger 18 may cause the rack 50 to move rearward (e.g., to the left in FIG. 2). The rack 50 may have teeth or other members which engage or interact with teeth or other members on the pinion gear 52. The teeth or members on the pinion gear 52 may also interact with teeth or other members on crown gear 54. Movement of the rack 50 may thus cause rotation of the pinion gear 52 which may further cause rotation of the crown gear 54. A coupling 58 couples the crown gear 54 to the catheter 60. Thus, rotation of the crown gear 54 causes rotation of the catheter 60. Although the actuation system 48 is described as a series of gears, any actuation system which converts the linear motion of the trigger 18 to rotational movement of the catheter 60 is contemplated.

The rack 50 may allow for 360° rotation of the pinion gear 52. Alternatively, the rack 50 may allow for a fraction of 360° rotation, such as, for example, 180° rotation, 90° rotation, 270° rotation, or anywhere between 0° rotation and 360° rotation. For example, the rack may be sized such that actuation of the rack 50 along the pinion gear 52 may allow for only partial rotation of the pinion gear 52. The rack 50 and trigger 18 may not allow for continuous spinning of the catheter 60. For example, the trigger 18 and rack 50 may be sized and arranged such that a single pull of the trigger 18 moves the rack 50 a discrete distance along the pinion gear 52. Additional pulls of the trigger 18 may thus be required to continue movement of the rack 50 and thus rotation of the pinion gear 52. Thus, to continue to rotate the catheter 60, the trigger 18 may be depressed and released continuously to effectuate multiple actuations of the actuation system 48. Alternatively, continuous rotation of the catheter 60 with a single pull of the trigger 18 may be provided.

The device 10 may be arranged such that depressing the trigger 18 effectuates rotation in one direction (e.g., clockwise or counter-clockwise) and release of the trigger 18 and the biasing member 20 pushing the trigger 18 into the normal, rest position may effectuate rotation in the opposite direction (e.g., the opposite of clockwise or counter-clockwise). This effect may be caused by the rack 50 moving backward, causing rotation of the pinion gear 52 in a first direction when the trigger 18 is depressed and the rack 50 moving forward when the biasing member 20 pushes the trigger 18 and thus the rack 50, causing rotation of the pinion gear 52 in a second direction, opposite to the first direction. The alternation of the direction of rotation of the catheter 60 caused by the alternating rotation of the actuation system 48 may assist in kicking-up or dislodging material near the catheter tip. Alternatively, the device 10 may cause rotation in a single direction, continuous non-stopping rotation in a single direction (e.g., rotation until cessation by a stopping device), and/or continuous non-stopping rotation in multiple directions.

Rotation of the catheter 60 before, after, or during suction of the device 10 may assist in dislodging or kicking-up the material near the distal tip of the catheter 60. This may assist in removing the material from the vasculature. The dam caused by the external cuff may prevent or prohibit material from traveling distal to the location of the distal tip of the catheter 60. This may assist in ensuring all material is evacuated with the device 10. Although the above is described with respect to a vasculature (e.g., an artery) of a lower extremity (e.g., a leg) of a patient, the method and device of the present disclosure may be employed in other locations and/or other vessels, such as for example, other limbs or locations of the patient that material may be desired to be removed and/or interventional procedures may be performed.

Although the device 10 is described in conjunction with an occluded vasculature, the device 10 may be employed in a vasculature that is not occluded. In an example, the device may be used in a purely thrombectomy procedure. The device 10 may be used in any procedure, whether or not the vasculature is occluded, that may benefit from the rotational and suction capabilities of the device 10. Additionally, although described in conjunction with an external cuff, the device 10 may be employed in a procedure where no cuff and/or no restriction to the flow in the vasculature is provided. In some examples, restriction to the flow may be provided in other manners than with an external cuff. In some examples, no restriction of flow may be desired.

The operational procedure and variations thereof described within the present disclosure may be achieved with any of the devices or any combination of features of the devices described herein.

Figure 4:
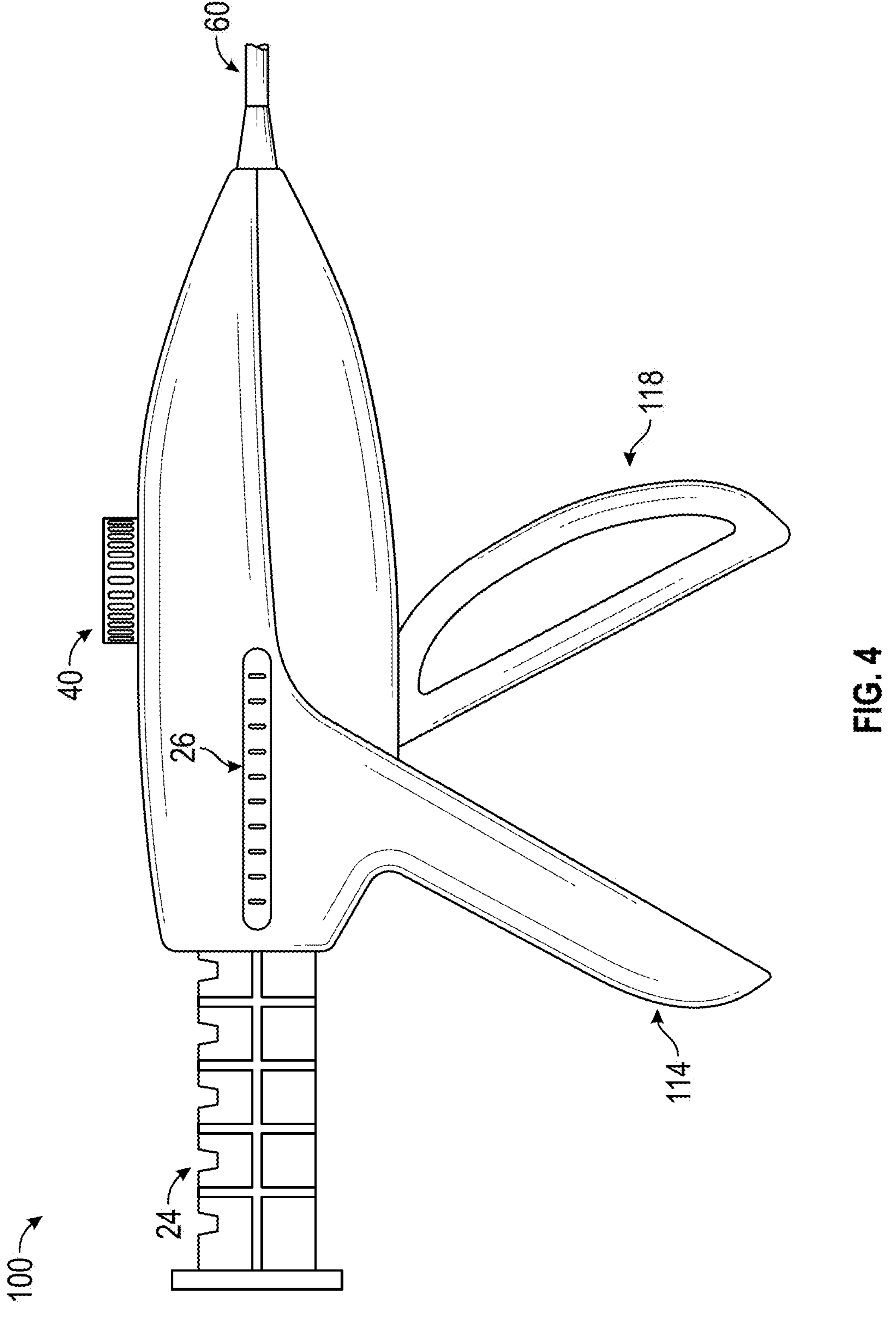
FIG. 4 shows an exemplary device, according to an embodiment of the present disclosure.
Figure 5:
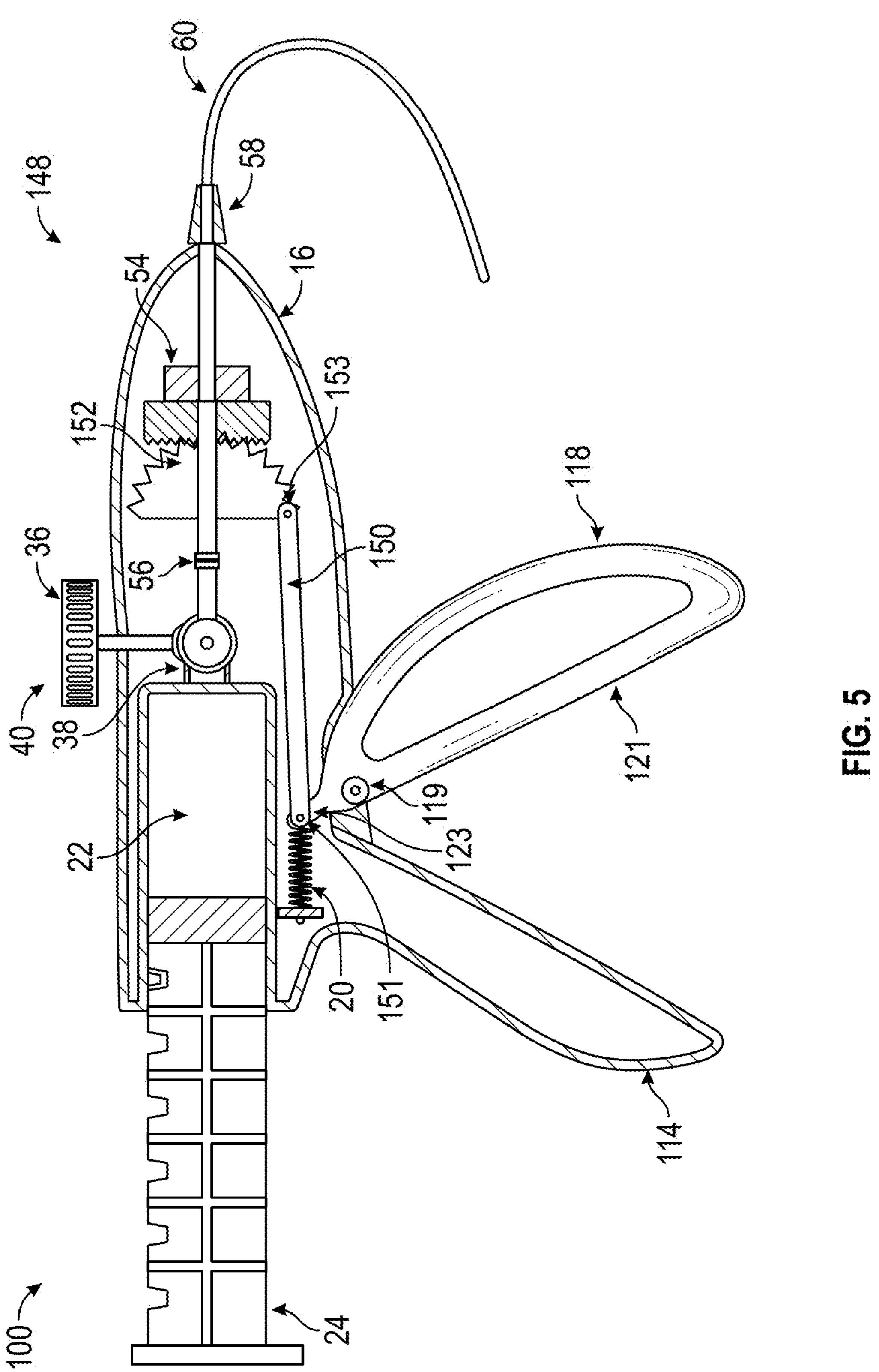
FIG. 5 shows a cross-sectional view of the exemplary device of FIG. 4, according to an embodiment of the present disclosure.

FIGS. 4 and 5 show an exemplary device 100. The exemplary device 100 may be the same or similar as the device 10 and similar numerals are relied upon to describe like components. Components not described in FIGS. 4 and 5 may be the same or similar as to like illustrated components in device 10. The device 100 may be used in the aforementioned method. The device 100 may include a handle 114 and a trigger 118. The trigger 118 may operate in a scissors action with respect to the handle 114. The trigger 118 may include a pivot 119. The pivot 119 may be a pin or other fastener or device which allows for a pivoting action of the trigger 118. The pivot 119 may be a high pivot point. The pivot 119 may be located within the housing 16. The pivot 119 may separate or define the trigger 118 into a handle portion 121 and a moment arm 123.

The device 100 may include an actuation system 148. The actuation system 148 may include a linkage 150, a half-moon gear 152, and a crown gear 54. The linkage 150, half-moon gear 152, and crown gear 54 may be selected based on the desired degree of rotation based on each depression of the trigger 118. The crown gear 54 may be a reduction gear. The crown gear 54 may be sized to achieve a desired number of rotations of the catheter 60 per actuation of the trigger 118. The smaller the crown gear 54, the more rotations of the catheter 60 may be achieved per actuation of the trigger 118.

To rotate the catheter 60, the user may depress the trigger 118. Biasing member 20 may be in a neutral state when the device 100 is not actuated. Depression of the trigger 118 may extend the biasing member 20. As the trigger 118 is operatively coupled to the linkage 150, depression of the trigger 118 may cause the linkage 150 to move forward (e.g., to the right in FIG. 5). The linkage 150 may be coupled at a first end 151 to the trigger 118 and at a second end 153 to the half moon gear 152. As the linkage 150 moves forward, the half moon gear 152 may rotate. In the example of FIG. 5, the rotation of the half moon gear 152 may be counter-clockwise. The half-moon gear 152 may have teeth or other members which engage or interact with teeth or other members on the crown gear 54. Movement of the linkage 150 may thus cause rotation of the half-moon gear 152 which may further cause rotation of the crown gear 54. A coupling 58 couples the crown gear 54 to the catheter 60.

Thus, rotation of the crown gear 54 causes rotation of the catheter 60. Although the actuation system 148 is described as a linkage and a series of gears, any actuation system which converts the linear motion of the trigger 118 to rotational movement of the catheter 60 is contemplated.

The linkage 150 may allow for full rotation of the half-moon gear 152 (e.g., 180° rotation). Alternatively, the linkage 150 may allow for a fraction of 180° rotation, such as, for example, 90° rotation, 45° rotation, or anywhere between 0° rotation and 180° rotation. The linkage 150 may not allow for continuous spinning of the catheter 60. Thus, to continue to rotate the catheter 60, the trigger 118 may be depressed and released continuously to effectuate multiple actuations of the actuation system 148. The device 100 may be arranged such that depressing the trigger 118 effectuates rotation in one direction (e.g., counter-clockwise as shown in FIG. 5) and release of the trigger 118, and the biasing member 20 moving from the extended, actuated state to the neutral, rest state pulling the trigger 118 into the normal, rest position may effectuate rotation in the opposite direction (e.g., clockwise). This effect may be caused by the linkage 150 moving forward, causing rotation of the half-moon gear 152 in a first direction when the trigger 118 is depressed and the linkage 150 moving backward when the biasing member 20 pulls the linkage 150, causing rotation of the half-moon gear 152 in a second direction, opposite to the first direction. The alternation of the direction of rotation of the catheter 60 caused by the alternating rotation of the actuation system 148 may assist in kicking-up or dislodging material near the catheter tip. Alternatively, the device 100 may cause rotation in a single direction, continuous non-stopping rotation in a single direction (e.g., rotation until cessation by a stopping device), and/or continuous non-stopping rotation in multiple directions.

Figures 6A, 6B, 6C:
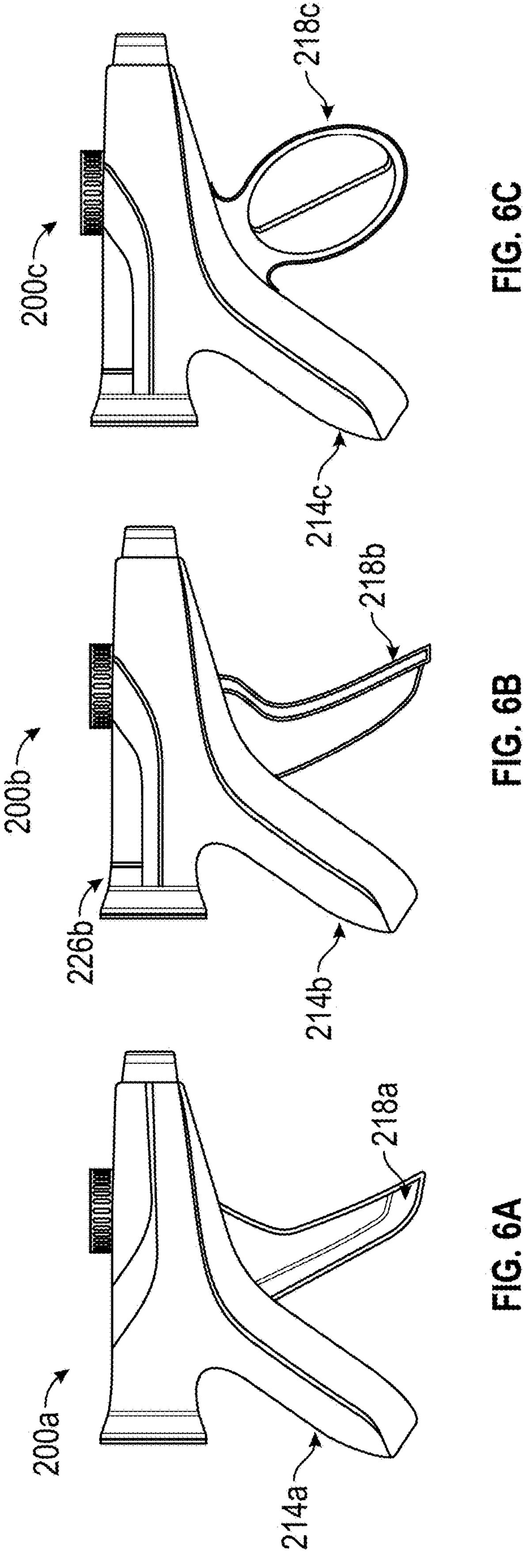
FIG. 6A shows an exemplary device, according to embodiments of the present disclosure.
FIG. 6B shows an exemplary device, according to embodiments of the present disclosure.
FIG. 6C shows an exemplary device, according to embodiments of the present disclosure.

FIGS. 6A-6C show exemplary devices 200*a*, 200*b*, and 200*c*, respectively. The device 200*a* of FIG. 6A may include a handle 214*a* and a trigger 218*a*. The handle 214*a* may be a main handle that is cored out. The trigger 218*a* may be a lever handle that fits inside the cored-out portion of the handle 214*a*. This may allow for maximized travel of the trigger, resulting in a greater or maximized degree of rotation of the gears and, in turn, a greater rotation of the catheter (not shown) per actuation of the trigger 218*a*. The device 200*b* of FIG. 6B may include a handle 214*b* and a trigger 218*b*. The handle 214*a* may be a paddle handle. The trigger 218*b* may be a blade-type trigger that recesses into the handle 214*b*. The device 200*b* may include a window 226*b* that is open on a top surface of the device 200*b*. The device 200*c* of FIG. 6C may include a handle 214*c* and a trigger 218*c*. The trigger 218*c* may be a full loop handle. In each of the devices 200*a*, 200*b*, and 200*c*, the triggers may include high pivot points to enable actuation of the actuating system, such as actuation system 148 of FIG. 5. Thus, any of the example devices of FIGS. 6A-6C may be used with the features of the device 100 or any of the devices described herein.

Figure 7:
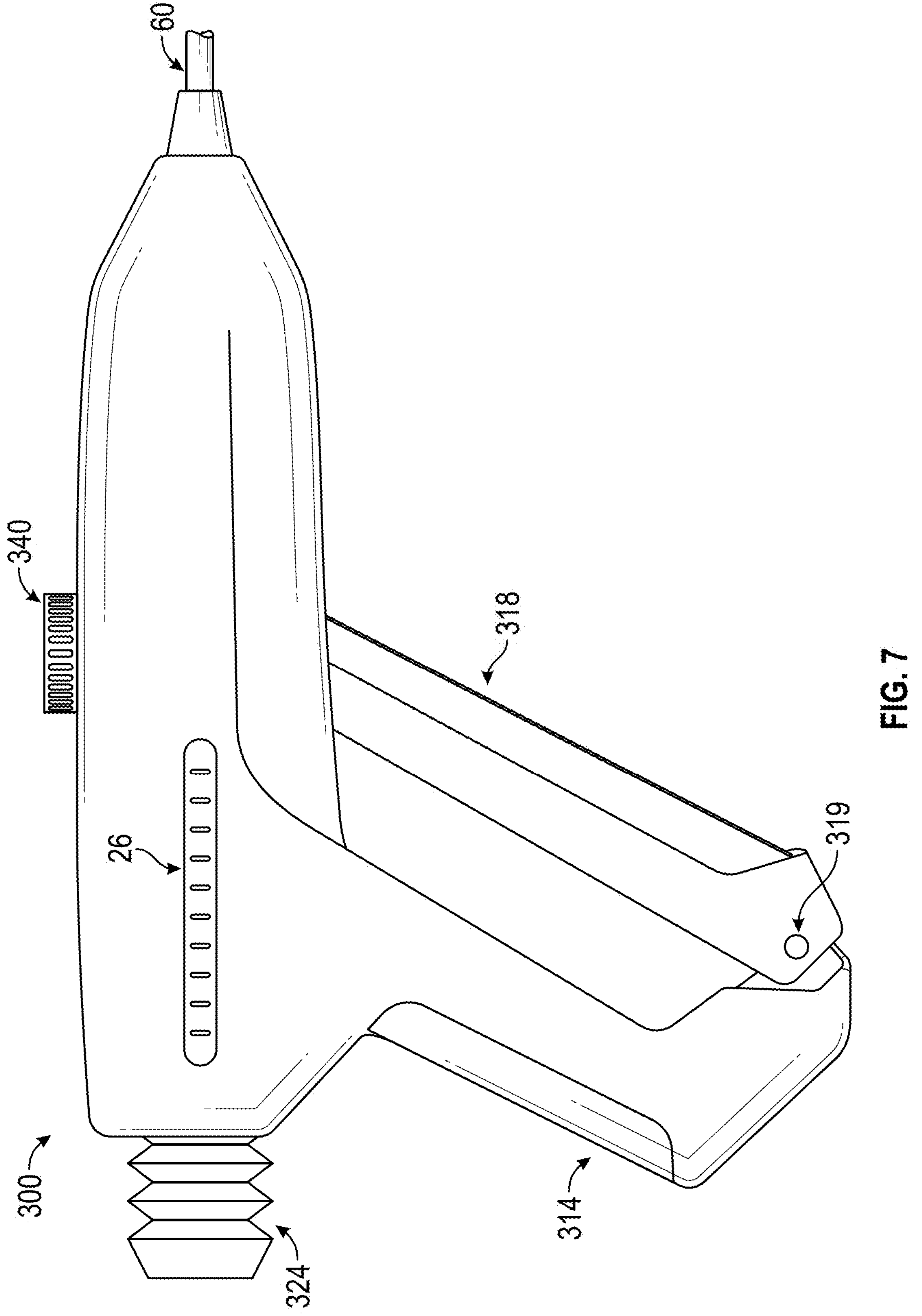
FIG. 7 shows an exemplary device, according to an embodiment of the present disclosure.
Figure 8:
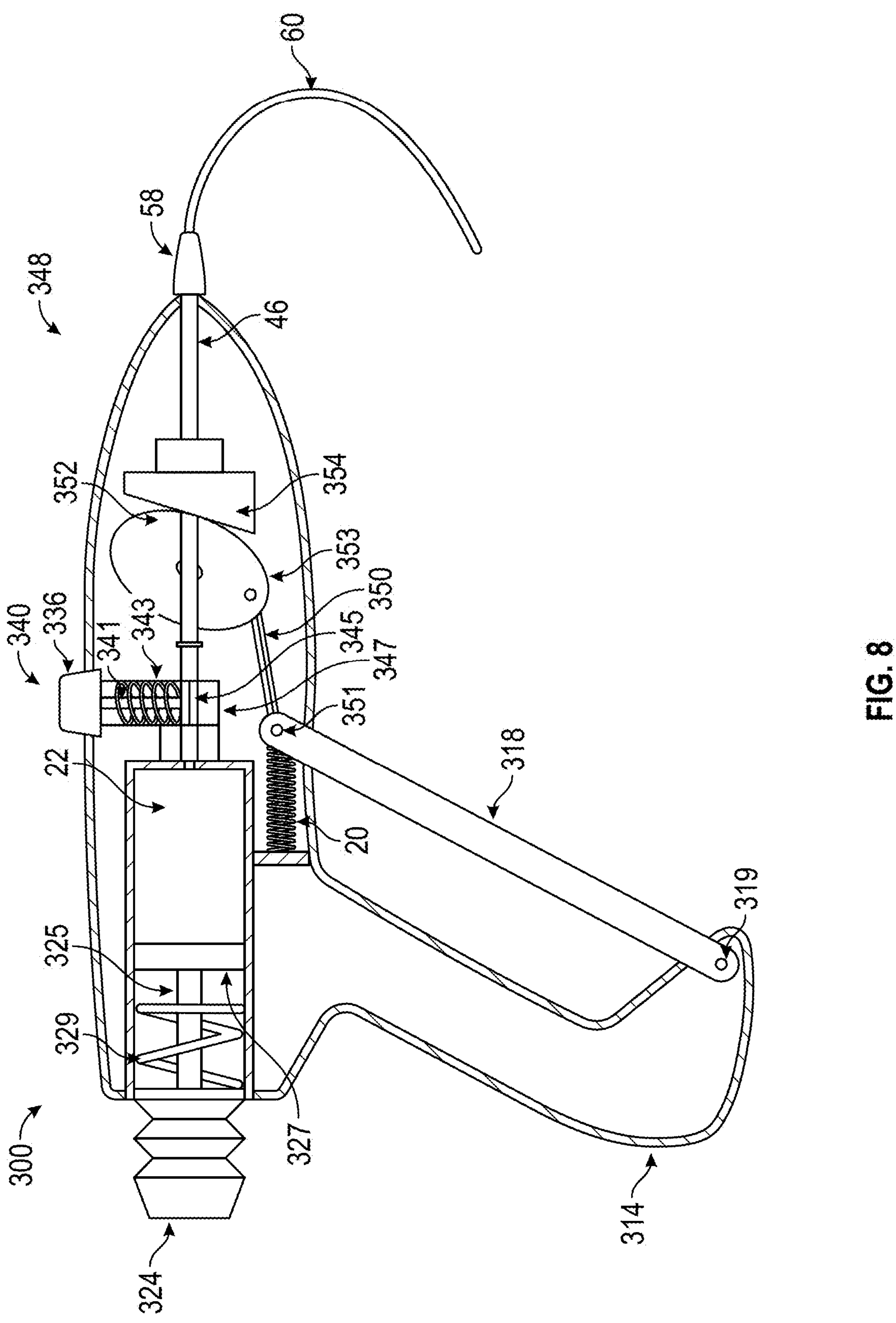
FIG. 8 shows a cross-sectional view of the exemplary device of FIG. 7, according to an embodiment of the present disclosure.

FIGS. 7 and 8 show an exemplary device 300. The exemplary device 300 may be the same or similar as the device 10 and similar numerals are relied upon to describe like components. Components not described in FIGS. 7 and 8 may be the same or similar as to like illustrated components in device 10. The device 300 may be used in the aforementioned method. The device 300 may include a handle 314 and a trigger 318. The trigger may include a pivot 319. The pivot 319 may be a pin or other fastener or device which allows for a pivoting action of the trigger 318. The pivot 319 may be a low pivot point. The pivot 319 may be located within the handle 314.

The device 300 may include a valve 336. The valve 336 may be a push release valve. The valve 336 may include a button 340, a shaft 341, a biasing member 343, and a valve member 345. The valve 336 may be biased to a normally closed position. That is, the valve member 345 may be biased by the biasing member 343 to obstruct the lumen 46 of the device 300. To open the valve 336, a user may depress the button 340 against the force of the biasing member 343 such that the shaft 341 moves the valve member 345 into a space 347 located adjacent to the lumen 46, thus permitting flow from the lumen 46 through the one-way valve 38 and into the chamber 22. To close the valve 336, the user may depress the button 340. A latch or lock may hold the button 340 and thus the valve 336 in the open and/or closed position.

The device 300 may include a bellows 324. The bellows 324 may be coupled to a shaft 325 and piston 327. A biasing member 329 may also be included. The shaft 325, piston 327, and biasing member 329 may be located within the chamber 22. To remove air from the chamber 22 to create the vacuum or negative pressure in the chamber, a user may pump or repeatedly press the bellows 324 to evacuate the air from the chamber 22 out of an opening in a distal end of the bellows (not visible). The opening may be a one-way opening that permits removal of air from the chamber 22 but does not allow air to travel through the bellows 324 and into the chamber 22. Pressing the bellows 324 inward (e.g., to the right in FIG. 8), extends the shaft 325, piston 327, and biasing member 329 into the chamber 22. When the bellows 324 is released, the biasing member 329 may move from the extended position to the neutral position. This action may cause the piston 327 to pull air out of the chamber 22 through the opening in the bellows 324. Repeated actuation of the bellows operates the system as a pump to remove air from the chamber 22 and create a vacuum therein. As in prior examples, the valve 336 is closed during the creation of the vacuum in the chamber 22.

The device 300 may include an actuation system 348. The actuation system 348 may include a linkage 350, a cam 352, and a cam follower 354. The linkage 350, cam 352, and cam follower 354 may be selected based on the desired degree of rotation based on each depression of the trigger 318. The cam 352 and cam follower 354 may be sized to achieve a desired number of rotations of the catheter 60 per actuation of the trigger 318.

To rotate the catheter 60, the user may depress the trigger 318. Biasing member 20 may be in a neutral state when the device 300 is not actuated. Depression of the trigger 318 may extend the biasing member 20. As the trigger 318 is operatively coupled to the linkage 350, depression of the trigger 318 may cause the linkage 350 to move forward (e.g., to the right in FIG. 8) The linkage 350 may be coupled at a first end 351 to the trigger 318 and at a second end 353 to the cam 352. As the linkage 350 moves forward, the cam 352 may rotate. In the example of FIG. 8, the rotation of the cam 352 may be counterclockwise. The cam 352 may have a profile or shape which mates, engages or interacts with a profile or shape of the cam follower 354. Movement of the linkage 350 may thus cause rotation of the cam 352 which may further cause rotation of the cam follower 354. A coupling 58 couples the cam follower 354 to the catheter 60. Thus, rotation of the cam follower 354 causes rotation of the catheter 60. Although the actuation system 348 is described as a linkage and cam arrangement, any actuation system which converts the linear motion of the trigger 318 to rotational movement of the catheter 60 is contemplated.

The linkage 350 may allow for full rotation of the cam 352 (e.g., 360° rotation). Alternatively, the linkage 350 may allow for a fraction of 360° rotation, such as, for example, 180° rotation, 270° rotation, 90° rotation, 45° rotation, or anywhere between 0° rotation and 360° rotation. The linkage 350 may not allow for continuous spinning of the catheter 60. Thus, to continue to rotate the catheter 60, the trigger 318 may be depressed and released continuously to effectuate multiple actuations of the actuation system 348. The device 300 may be arranged such that depressing the trigger 318 effectuates rotation in one direction (e.g., counter-clockwise as shown in FIG. 8) and release of the trigger 318, and the biasing member 20 moving from the extended, actuated state to the neutral, rest state pulling the trigger 318 into the normal, rest position may effectuate rotation in the opposite direction (e.g., clockwise). This effect may be caused by the linkage 350 moving forward, causing rotation of the cam 352 in a first direction when the trigger 318 is depressed and the linkage 350 moving backward when the biasing member 20 pulls the linkage 350, causing rotation of the cam 352 in a second direction, opposite to the first direction. The alternation of the direction of rotation of the catheter 60 caused by the alternating rotation of the actuation system 348 may assist in kicking-up or dislodging material near the catheter tip. Alternatively, the device 300 may cause rotation in a single direction, continuous non-stopping rotation in a single direction (e.g., rotation until cessation by a stopping device), and/or continuous non-stopping rotation in multiple directions.

Figure 9:
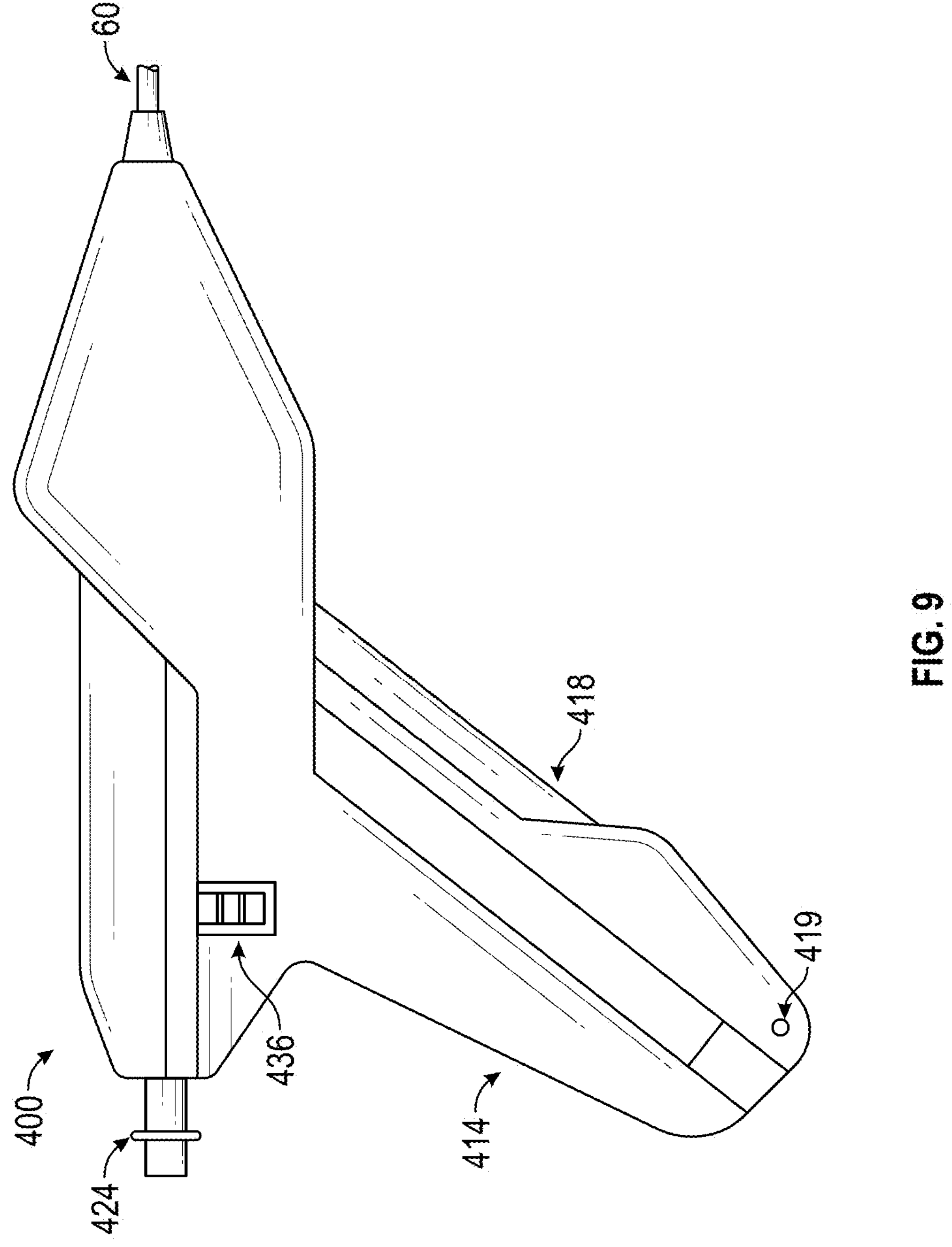
FIG. 9 shows an exemplary device, according to an embodiment of the present disclosure.
Figure 10:
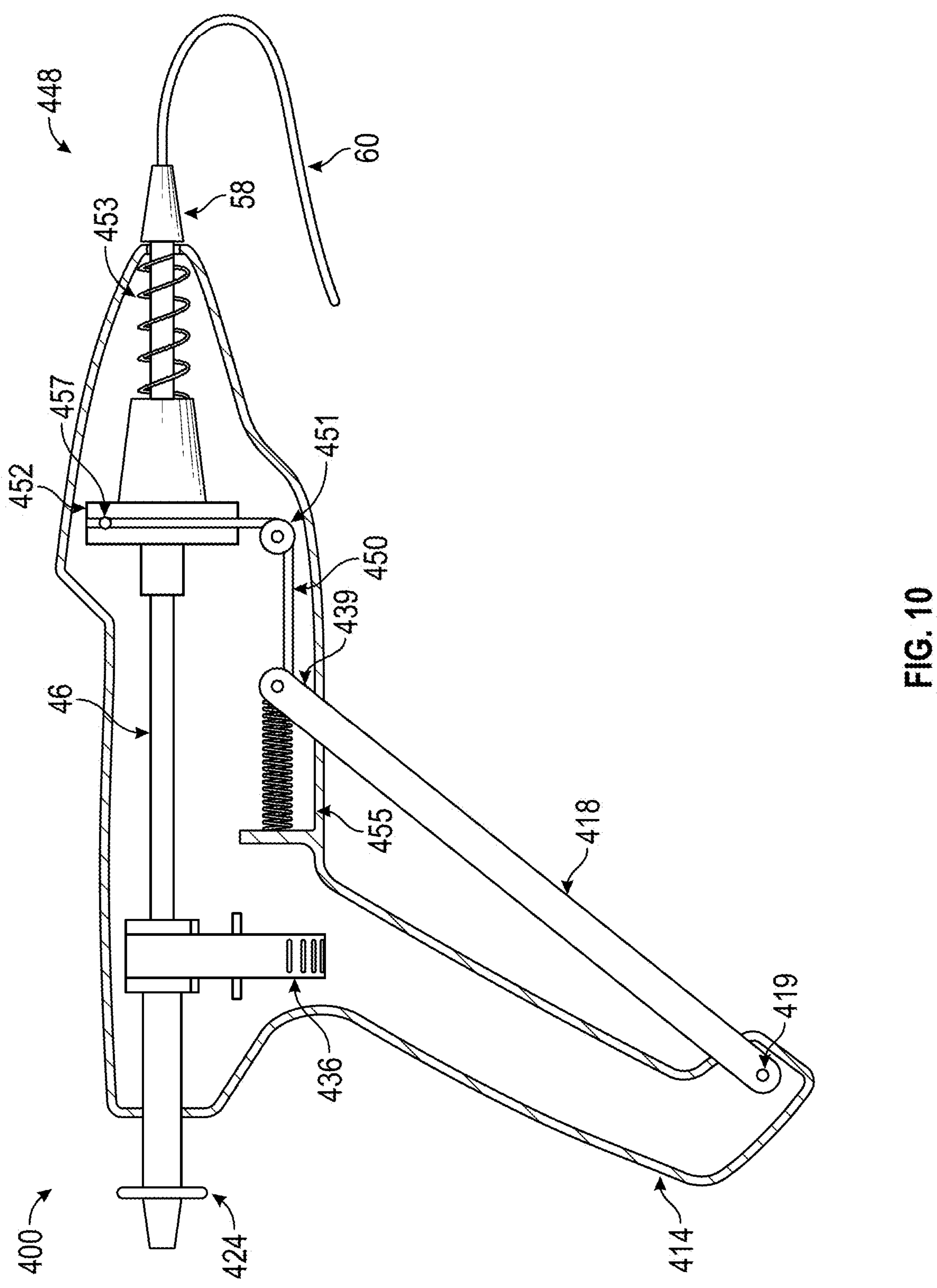
FIG. 10 shows a cross-sectional view of the exemplary device of FIG. 9, according to an embodiment of the present disclosure.
Figures 11A, 11B, 11C, 11D, 11E, 11F:
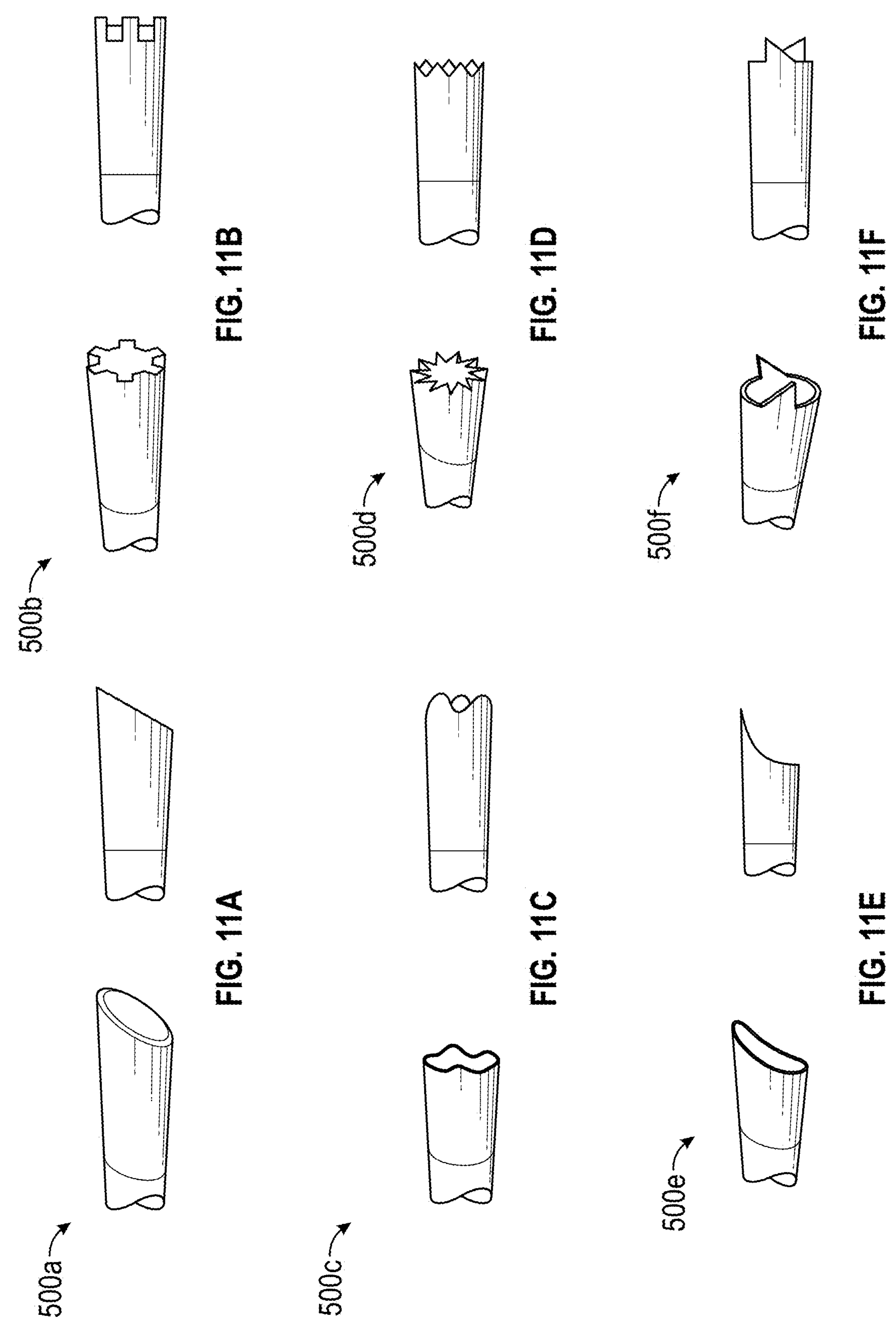
FIGS. 11A-11F show exemplary catheter tips for use in a device, according to an embodiment of the present disclosure.

FIGS. 9 and 10 show an exemplary device 400. The exemplary device 400 may be the same or similar as the device 10 and similar numerals are relied upon to describe like components. Components not described in FIGS. 9 and 10 may be the same or similar as to like illustrated components in device 10. The device 400 may be used in the aforementioned method. The device 400 may include a handle 414 and a trigger 418. The trigger may include a pivot 419. The pivot 419 may be a pin or other fastener or device which allows for a pivoting action of the trigger 418. The pivot 419 may be a low pivot point. The pivot 419 may be located within the handle 414.

The device 400 may include a pressure release 436. The pressure release 436 may be a thumb actuated pressure release. The pressure release 436 may be a single hand actuation. The pressure release 436 may be biased to a closed position. The pressure release 436 may be a normally closed valve. In an embodiment, the pressure release 436 may be the same or similar as the valve 336 of FIG. 8. The pressure release 436 may be a wheel or other rotating member. The pressure release 436 may include an opening in a portion thereof that extends through the pressure release 436. When the opening is aligned with the lumen 46, fluid may be allowed to flow through the catheter 60, lumen 46 and out of the device 400 via a barb 424. When the opening is misaligned with the lumen 46, that is, when a solid portion of the pressure release 436 is aligned in the lumen 46 blocking the pathway, no fluid may be allowed to flow through the lumen 46.

The device 400 may include a barb 424. The barb 424 may be a suction barb, such as a wall suction barb. The barb 424 may allow for coupling the device 400 to a supplied suction (not shown). Thus, barb 424 may allow for suction when the supplied suction (e.g., via a vacuum device) is applied to barb 424. In some examples, the on-demand suction may occur whenever the device is turned on and off as suction is needed and the pressure release 436 may be held in the open position. In some examples, the on-demand suction may occur when the device is held in an on position and the pressure release 436 is opened and closed when suction is desired.

The device 400 may include an actuation system 448. The actuation system 448 may include a cable drive system. The actuation system 448 may include a cable 450, a post 451, a spindle 452, and a return spring 453. A cable assist 455 may optionally be provided. The post 451 may be a pulley or device that allows for force to be transferred from the pull of the trigger 418 to the spindle 452. The spindle 452 may be a wheel. The spindle 452 and/or the cable 450 may be selected based on the desired degree of rotation based on each depression of the trigger 418. The spindle 452 may be sized to achieve a desired number of rotations of the catheter 60 per actuation of the trigger 418. The number of rotations per pull of the trigger 418 may be directly correlated to the diameter of the spindle 452. The cable 450 may be wrapped around a groove or depression in the outer diameter of the spindle 452. In an example, the cable 450 may be wrapped multiple times around the outer diameter of the spindle 452 to allow for multiple rotations of the catheter 60 per pull of the trigger 418.

To rotate the catheter 60, the user may depress the trigger 418. As the trigger 418 is operatively coupled to the cable 450, depression of the trigger 418 may cause the cable 450 to move rearward (e.g., to the left in FIG. 10). The cable 450 may be coupled at a first end 439 to the trigger 418 and at a second end 457 to the spindle 452. The cable 450 may extend around the post 451 at a position between the first end 439 and the second end 457. As the cable moves rearward, the spindle 452 may rotate until the cable 450 is no longer wrapped around the outer diameter of the spindle 452. Movement of the cable 450 may thus cause rotation of the spindle 452. A coupling 58 couples the spindle 452 to the catheter 60. Thus, rotation of the spindle 452 causes rotation of the catheter 60. Although the actuation system 448 is described as cable arrangement, any actuation system which converts the linear motion of the trigger 418 to rotational movement of the catheter 60 is contemplated. When the trigger 418 is no longer depressed, the return spring 453 may rotate the spindle 452 back to a rest or neutral position. This may cause the cable 450 to wrap around the outer diameter of the spindle 452, pulling the trigger 418 back into the neutral position. The cable assist 455 may be a biasing member that may assist in returning the cable to the neutral position. The return spring 453 may cause the spindle 452 to rotate in an opposite direction as compared to the direction of rotation during actuation of the trigger 418.

The cable 450 may allow for full rotation of the spindle 452 (e.g., 360° rotation). Alternatively, the cable 450 may allow for a fraction of 360° rotation, such as, for example, 180° rotation, 270° rotation, 90° rotation, 45° rotation, or anywhere between 0° rotation and 360° rotation and/or for multiples of rotation of the spindle 452 (e.g., 540° rotation). The cable 450 may not allow for continuous spinning of the catheter 60. Thus, to continue to rotate the catheter 60, the trigger 418 may be depressed and released continuously to effectuate multiple actuations of the actuation system 448. The device 400 may be arranged such that depressing the trigger 418 effectuates rotation in one direction (e.g., clockwise as shown in FIG. 10) and release of the trigger 418, and the motion of the return spring 453, may effectuate rotation in the opposite direction (e.g., counter-clockwise). This effect may be caused by the cable 450 moving backward, causing rotation of the spindle 452 in a first direction when the trigger 418 is depressed and the cable 450 moving backward when the return spring 453 pulls the cable 450 back onto the spindle 452, causing rotation of the spindle 452 in a second direction, opposite to the first direction. The alternation of the direction of rotation of the catheter 60 caused by the alternating rotation of the actuation system 448 may assist in kicking-up or dislodging material near the catheter tip. Alternatively, the device 400 may cause rotation in a single direction, continuous non-stopping rotation in a single direction (e.g., rotation until cessation by a stopping device), and/or continuous non-stopping rotation in multiple directions.

FIGS. 151A-15F show various catheter tips for the catheter 60. The tips 500*a*, 500*b*, 500*c*, 500*d*, 500*e*, and 500*f* may be selected based on the desired function of the tip, the particular environment in which the catheter is deployed, the interventional procedure, if any, performed, and the amount of force needed at the distal tip to dislodge the material. The tip 500*a* may be a chiseled tip. The tip 500*b* may be a castle tip. The tip 500*c* may be a wave tip. The tip 500*d* may be a saw tip. The tip 500*e* may be a scallop tip. The tip 500*f* may be a knife tip. One or more of the tips may assist in removal of material from the vasculature.

An exemplary actuation system that may be employed to allow for continuous rotation of the catheter may be a barrel cam. A barrel cam may be a device having a cam path extending around a circumference of a barrel and a cam follower pin configured to engage the cam path. The linear movement caused by actuation of the trigger may engage a cam follower pin that is spring loaded to engage the cam path on the face of the barrel. The cam path of the barrel may be a recessed path that translates the linear movement of the cam follower pin to rotational movement around the catheter axis. The cam path may be stepped to provide only one continuous path for the spring-loaded cam follower pin to follow and thus may provide continuous rotation in a single direction to the barrel. Connecting the catheter directly to the cannulated barrel may in turn rotate the catheter continuously. Other linear to rotational conversion devices may be employed to allow for continuous rotation of the catheter and/or intermittent rotation of the catheter as described previously.

Any of the features of the devices described herein may exchange or replace any of the other features in the devices without departing from the disclosure. For example, the trigger of device 100 may be used in device 10, 200, 300, 400, 700, and 800 and vice-versa. Likewise, the actuation system of device 100 may be used in any of devices 10, 200, 300, 400, 700, and 800 and vice-versa.

Figure 12:
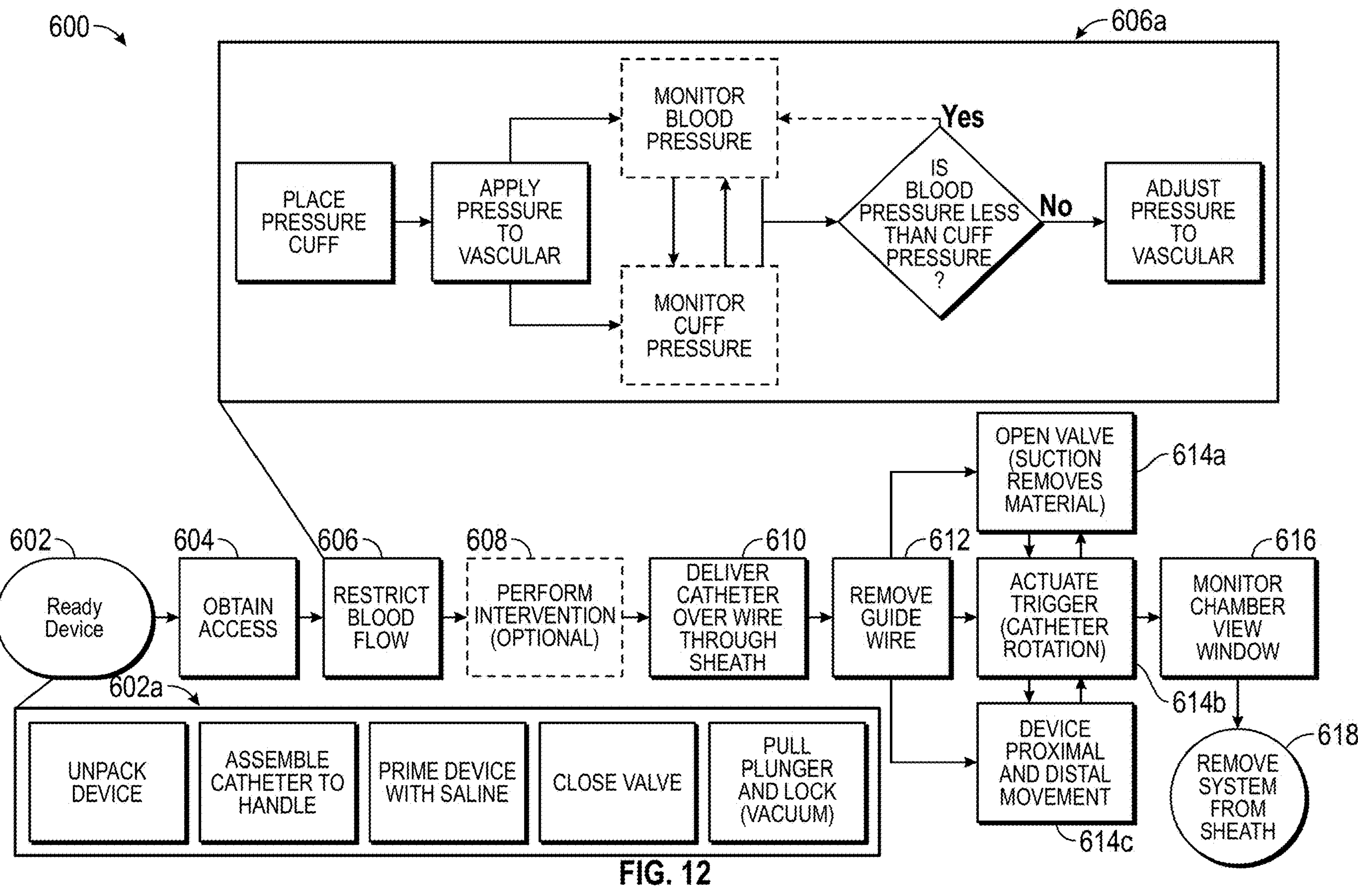
FIG. 12 shows a method, according to an embodiment of the present disclosure.

FIG. 12 shows an exemplary process 600 for using any of the devices described herein. In step 602, the device (e.g., device 10) may be readied for use. Step 602 may further include any or all of sub-steps 602*a*, including, but not limited to, unpacking the device, assembling the catheter to the handle, priming the device with saline, closing the valve (e.g., valve 36), and/or creating the vacuum (e.g., pulling and locking the plunger). After readying of the device, the user (e.g., a physician), at step 604, may obtain access to the vasculature to be treated. The user may create a restriction in blood flow at step 606. Alternatively, the restriction in blood flow at step 606 may be performed prior to gaining access in step 604. The restriction in blood flow created at step 606 may include any or all of sub-steps 606*a*, including, but not limited to, placing a pressure cuff, applying pressure to the vasculature, monitoring blood pressure, monitoring cuff pressure, adjusting pressure in the vasculature based on the blood pressure measured and/or based on the cuff pressure monitored. For example, if the blood pressure is not less than the cuff pressure, then the pressure in vasculature may be adjusted.

With continued reference to FIG. 12, the user may perform an interventional procedure at step 608. As discussed previously, this step may be optional and the user may instead use the device 10 without an interventional device such as used in step 608.

The user, at step 610, may deliver the catheter (e.g., catheter 60) of the device over a guidewire and through a sheath and at step 612, may remove the guidewire. Step 612 may be optional and the guidewire may remain during use of the device. With the device in the proper location, the user may begin operation of the device. This may include opening the valve to initiate the suction to remove material at step 614*a*, actuating the trigger to initiate rotation of the catheter at step 614*b*, and/or moving the device longitudinally to and fro (e.g., proximal and distal movement) at step 614*c*. Any or all of steps 614*a*, 614*b*, and 614*c* may be performed, in any order, sequentially, simultaneously, or may be omitted.

At step 616, the chamber (by way of the view window) may be monitored for collection of materials. When the desired amount of material is removed, the user may remove the system from the sheath at step 618. The procedure may be repeated as necessary at the same or different locations. When completed, the cuff may be removed. If, in step 616, the chamber is completely filled, the chamber may be emptied and a suction re-established to continue removal of material as necessary.

Figure 13:
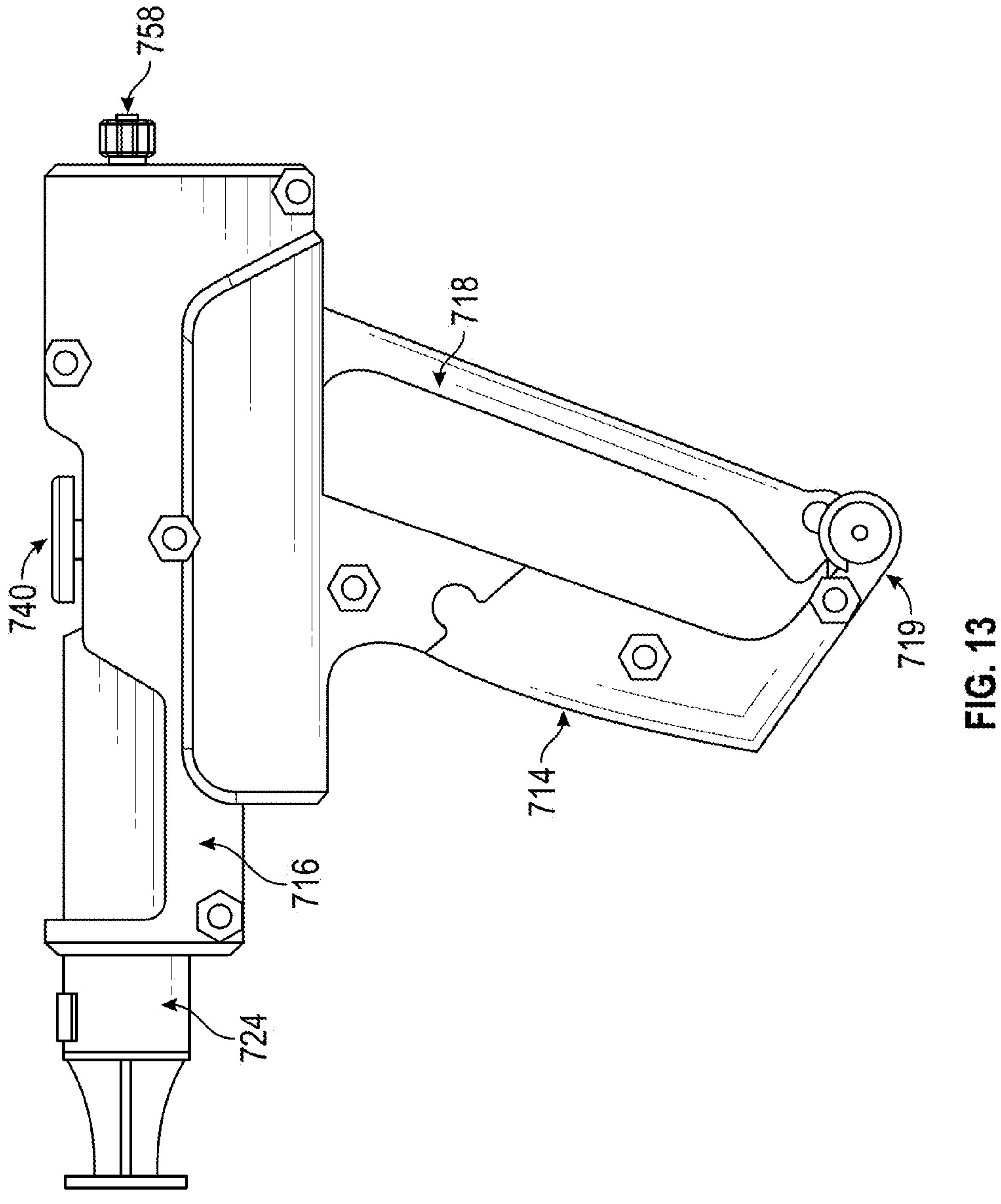
FIG. 13 shows an exemplary device, according to an embodiment of the present disclosure.
Figure 14:
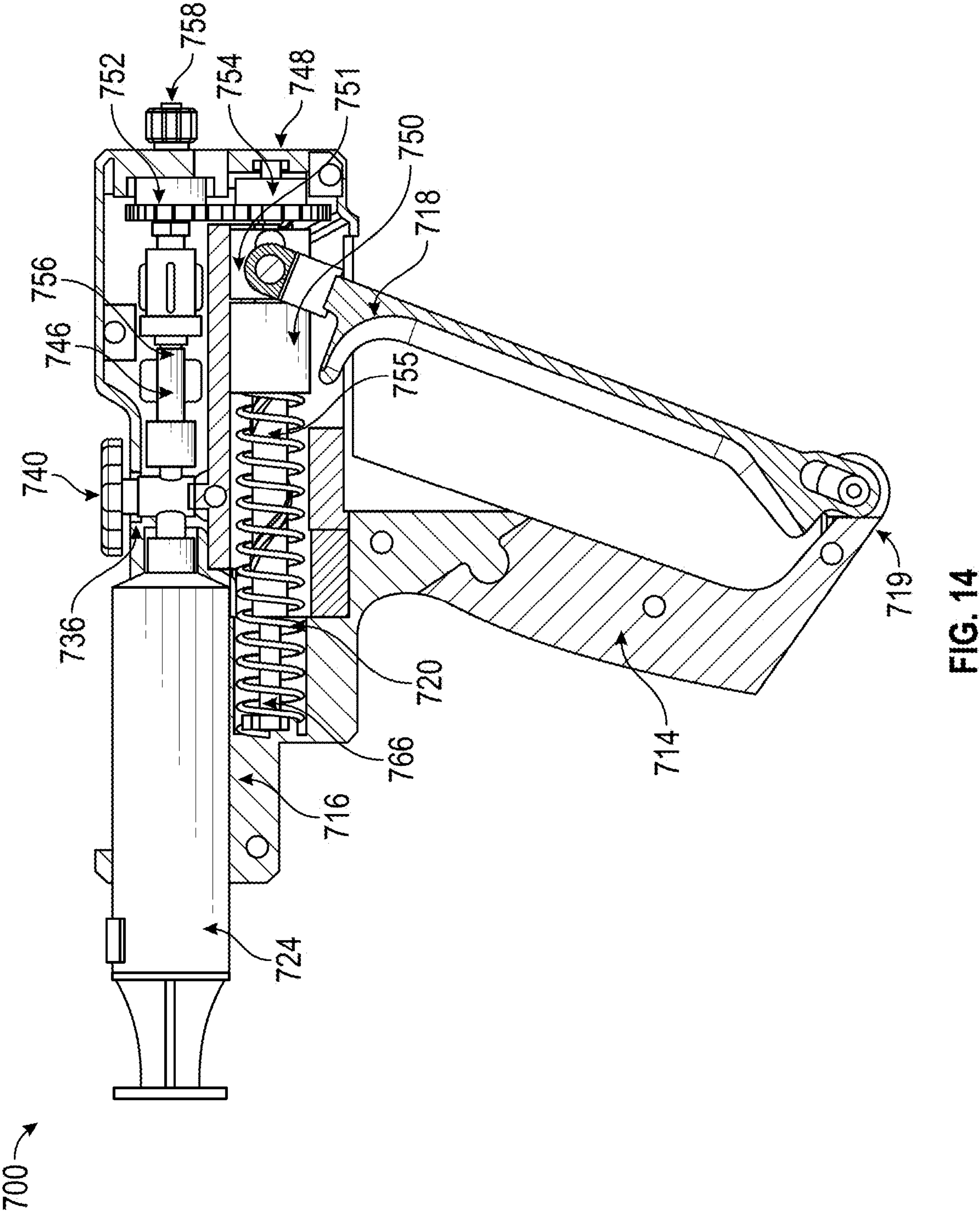
FIG. 14 shows a cross-sectional view of the exemplary device of FIG. 13, according to an embodiment of the present disclosure.

FIGS. 13 and 14 show another exemplary device 700. According to this embodiment, a helical screw pattern is utilized to transmit linear motion of the trigger 718 into rotational motion of a gear/driver 752, as described in further detail below. One of the advantages of this embodiment, is that the liquid flow path or lumen 746 is separated from the actuation system 748 or rotational drive mechanism that includes a helix 755 and shuttles 750, 751 by a gear set 752, 754. This reduces the complexity of the rotating components and ensures that the rotational components do not pass bodily fluids and are, therefore, not required to meet the same biocompatibility requirements as the liquid path.

The exemplary device 700 of FIGS. 13 and 14 may be the same or similar as the device 10 and similar numerals are relied upon to describe like components. Components not described in FIGS. 13 and 14 may be the same or similar as to like illustrated components in device 10. The device 700 may be used in the aforementioned method. The device 700 may include a handle 714 and a trigger 718. The trigger 718 may include a pivot 719. The pivot 719 may be a pin or other fastener or device which allows for a pivoting action of the trigger 718. The pivot 719 may be a low pivot point. The pivot 719 may be located within the handle 714.

In this embodiment, the handle 714 includes the trigger 718 and a biasing member 720, in the form of a spring, such as a coil spring, although other biasing devices are contemplated. The biasing member 720 may begin in a neutral state to be compressed by the trigger 718 during actuation of the device 700. When force is released from the trigger 718, the compressed biasing member 720 may extend back to the neutral state.

The rotating component of the liquid flow path or lumen 746 of this embodiment is the gear/driver 752, which is separated from the valve 736 (e.g., a manual stop valve or non-rotating stopcock) and the plunger 724 (e.g., locking syringe) by a rotating seal 756. This rotating seal 756 is configured to provide a leak-free flow path along the lumen 746, while allowing free rotation between the ends of the device 700. The housing 716 supports and locates the components of the actuation system 748 or rotational drive mechanism and bearings/bushings may be added to reduce friction and ease rotation.

When the trigger 718 is actuated, it moves a free shuttle 751. The free shuttle 751 engages with and drives a drive shuttle 750, which features an internal helical pattern matching that of the helix 755. When the drive shuttle 750 passes over the helix 755, it causes the helix 755 to rotate around a drive shaft 766. This rotation spins the gear 754, which drives the gear/driver 752, to which a catheter is connected (see, e.g., catheter 60 of FIGS. 2 and 5) via a coupling 758. The biasing member 720 (e.g., compression spring) returns the shuttles 750, 751 and the trigger 718 to their starting positions at the front of the device 700 (i.e., the right side of the device 700 in FIG. 14) after each trigger actuation. The teeth by which the drive shuttle 750 and the free shuttle 751 engage can be configured such that only rotation in one direction is allowed. According to one embodiment, it is advantageous to the function of the actuation system 748 or rotational drive mechanism that the catheter (e.g., catheter 60) rotate unidirectionally, so as the biasing member 720 (e.g., compression spring) returns the shuttles 750, 751 and the trigger 718 to their starting positions, the drive shuttle 750 will rotate freely around the helix 755 without engaging the free shuttle 751 or causing the helix 755 or gear/driver 752 to rotate. This motion may be repeated throughout the duration of the aspiration.

According to this embodiment, the aspiration process is simplified by the integration of a plunger 724 (e.g., locking syringe) and a valve 736 (e.g., stopcock). To create vacuum pressure, the valve 736 (e.g., stopcock) is set to a "closed" position, by depressing knob 740, and plunger 724 (e.g., locking syringe) is drawn. Rotation of the plunger 724 (e.g., locking syringe) allows it to lock in place, resisting the closing force created by the vacuum. The user may then proceed with other aspects of the procedure. For example, to remove emboli, the user will begin rotation with one hand via the trigger 718 and subsequently open the valve 736 (e.g., stopcock) with the other hand, using the knob 740, to release suction and begin aspiration of emboli. The aforementioned features of the embodiment of the device illustrated in FIGS. 13 and 14 allow for separation of the mechanisms of suction and rotation, while allowing for simultaneous suction and rotation, with the ability to begin rotation prior to suction, in order to agitate/disperse emboli prior to aspiration.

Figure 15:
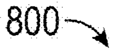
FIG. 15 shows an exemplary device, according to an embodiment of the present disclosure.
Figure 15:
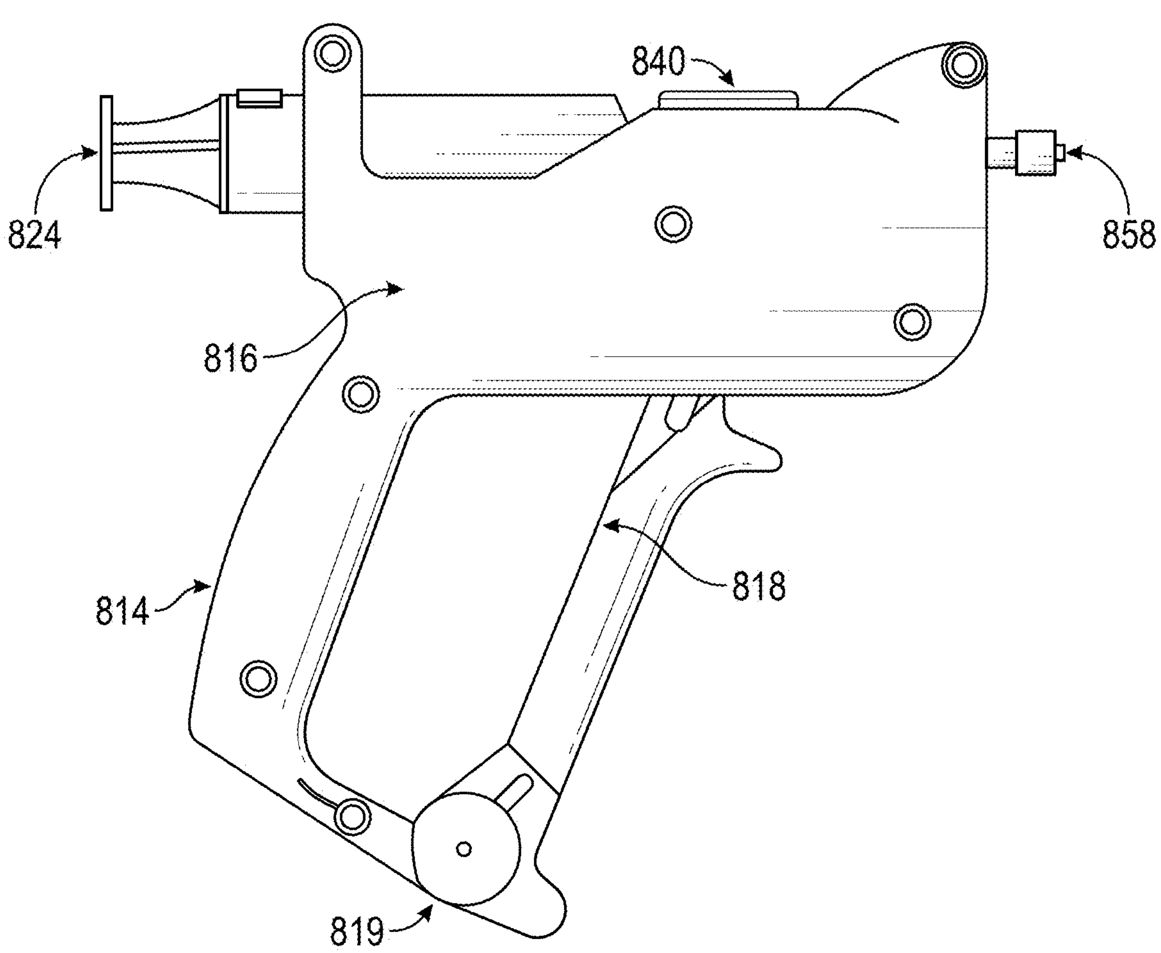
Figure 16:
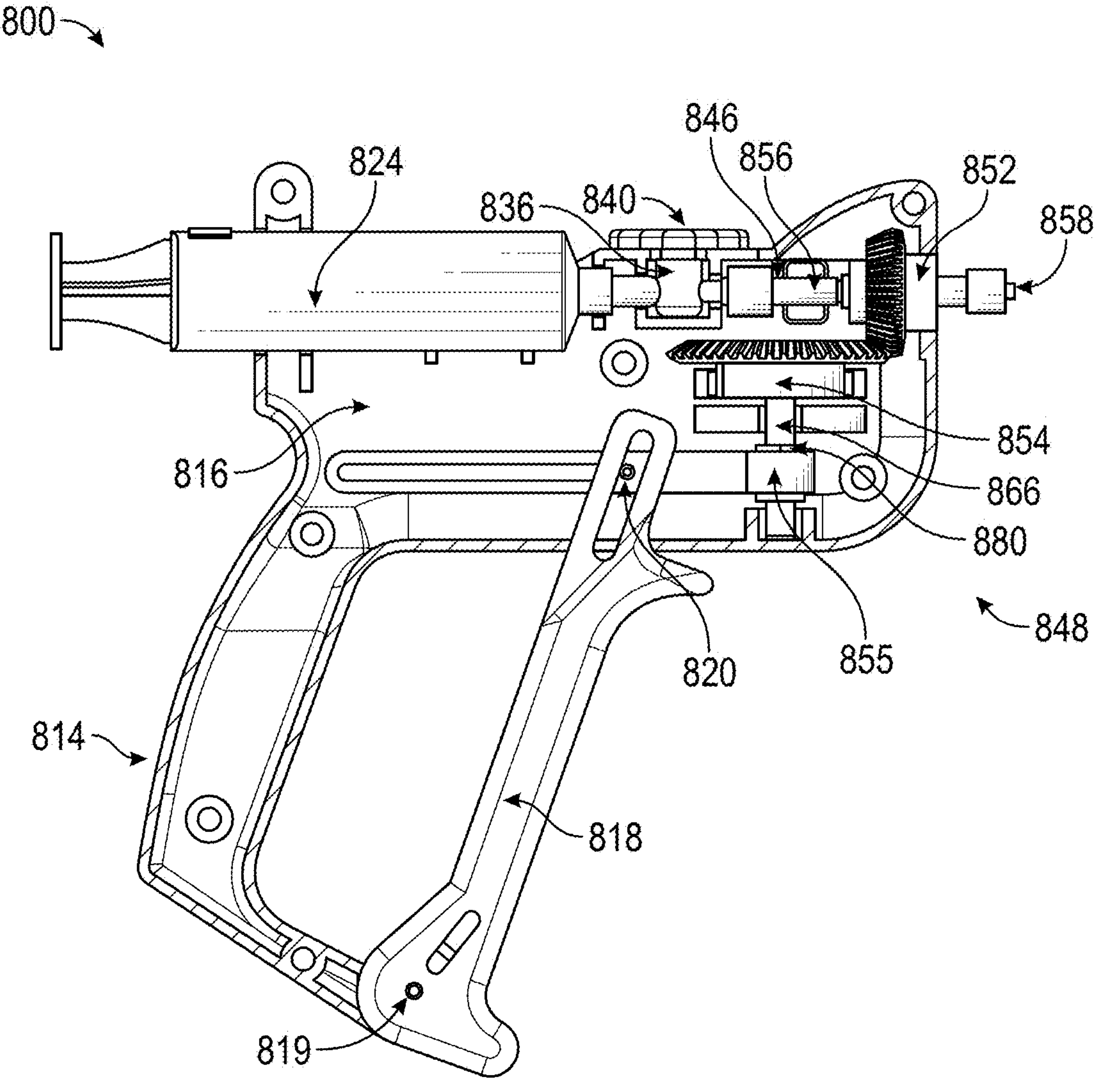
FIG. 16 shows a cross-sectional view of the exemplary device of FIG. 15, according to an embodiment of the present disclosure.

FIGS. 15 and 16 show another exemplary device 800. According to this embodiment, a bevel gear set 852, 854 is utilized, along with a constant force spring 855 and a one-way locking bearing 880 to transmit linear motion of the trigger 818 into rotational motion of a coupling 858 (e.g., luer adapter), which is generally attached to a catheter (see, e.g., catheter 60 of FIGS. 2 and 5). One of the advantages of this embodiment, is that the liquid flow path or lumen 846 is separated from the actuation system 848 or rotational drive mechanism that includes the constant-force spring 855 and one-way locking bearing 880. According to this embodiment, the complexity of the rotating components is reduced, while ensuring that the rotational components do not pass bodily fluids and are, therefore, not required to meet the same biocompatibility requirements as the liquid path.

The exemplary device 800 of FIGS. 15 and 16 may be the same or similar as the device 10 and similar numerals are relied upon to describe like components. Components not described in FIGS. 15 and 16 may be the same or similar as to like illustrated components in device 10. The device 800 may be used in the aforementioned method. The device 800 may include a handle 814 and a trigger 818. The trigger 818 may include a pivot 819. The pivot 819 may be a pin or other fastener or device which allows for a pivoting action of the trigger 818. The pivot 819 may be a low pivot point. The pivot 819 may be located within the handle 814.

In this embodiment, the handle 814 includes the trigger 818 and a biasing member 820, in the form of a pin, although other biasing devices are contemplated. The biasing member 820 (e.g., pin) may start at an initial position to be biased by the trigger 818 during actuation of the device 800. When force is released from the trigger 818, the biasing member 820 (e.g., pin) may return to its initial position.

The rotating component of the liquid flow path or lumen 846 of this embodiment is the coupling 858 (e.g., luer adapter). The coupling 858 is separated from the valve 836 (e.g., a manual stop valve or non-rotating stopcock) and the plunger 824 (e.g., locking syringe) by a rotating seal 856. The rotating seal 856 is configured to provide a leak-free flow path along the lumen 846, while allowing free rotation between the ends of the device 800. A small bevel gear 852 is fixed axially to the outside of one end of the rotating seal 856, which allows the gear 852 to drive rotation, while remaining separated from bodily fluids. The housing 816 supports/locates the components of the actuation system 848 or rotational drive mechanism and bearings/bushings may be added to reduce friction and ease rotation.

When the trigger 818 is actuated, it pulls/uncoils the constant-force spring 855, via the biasing member 820 (e.g., pin). The constant-force spring 855 is coiled around a one-way locking bearing 880. According to one embodiment, the one-way locking bearing 880 allows free rotation in one direction, but locks to prevent rotation in the other direction. The one-way bearing 880 is generally oriented such that it will lock in the direction of uncoiling of the constant-force spring 855. This locking of the one-way bearing 880 turns the drive shaft 866 and large bevel gear 854, which engages with and rotates the small bevel gear 852 to drive the coupling 858 (e.g., luer adapter) and any catheter (see, e.g., catheter 60 of FIGS. 2 and 5) to which the coupling 858 may be connected. According to one embodiment, it is advantageous to the function of the actuation system 848 or rotational drive mechanism that the catheter (e.g., catheter 60), via coupling 858 (e.g., luer adapter), rotates unidirectionally, so as the trigger 818 is returned to its starting position by the coiling force of the constant-force spring 855, the one-way locking bearing 880 will freely rotate about the drive shaft 866 and allow the constant-force spring 855 to coil without rotating the drive shaft 866 or any other rotating components. This motion may be repeated throughout the duration of the aspiration.

According to this embodiment, the aspiration process is simplified by the integration of a plunger 824 (e.g., locking syringe) and a valve 836 (e.g., stopcock). To create vacuum pressure, the valve 836 (e.g., stopcock) is set to a "closed" position, by depressing knob 840, and plunger 824 (e.g., locking syringe) is drawn. Rotation of the plunger 824 (e.g., locking syringe) allows it to lock in place, resisting the closing force created by the vacuum. The user may then proceed with other aspects of the procedure. For example, to remove emboli, the user will begin rotation with one hand via the trigger 818 and subsequently open the valve 836 (e.g., stopcock) with the other hand, using the knob 840, to release suction and begin aspiration of emboli. The aforementioned features of the embodiment of the device illustrated in FIGS. 15 and 16 allow for separation of the mechanisms of suction and rotation, while allowing for simultaneous suction and rotation, with the ability to begin rotation prior to suction, in order to agitate/disperse emboli prior to aspiration.

FIGS. 17 to 33 show another exemplary device 900. According to this embodiment, a helical screw pattern is utilized to transmit linear motion of the trigger 918 into rotational motion of a gear/driver 952, as described in further detail below. One of the advantages of this embodiment, is that the liquid flow path or lumen 946 is separated from the actuation system 948, also referred to as a rotational drive mechanism, that includes a gear set 952, 954 free shuttle 951, drive shuttle 950, slip ring 953, helix 955, and biasing member 920 by the gear set 952, 954. This reduces the complexity of the rotating components and ensures that the rotational components do not pass bodily fluids and are therefore not required to meet the same biocompatibility requirements as the liquid path.

Figure 17:
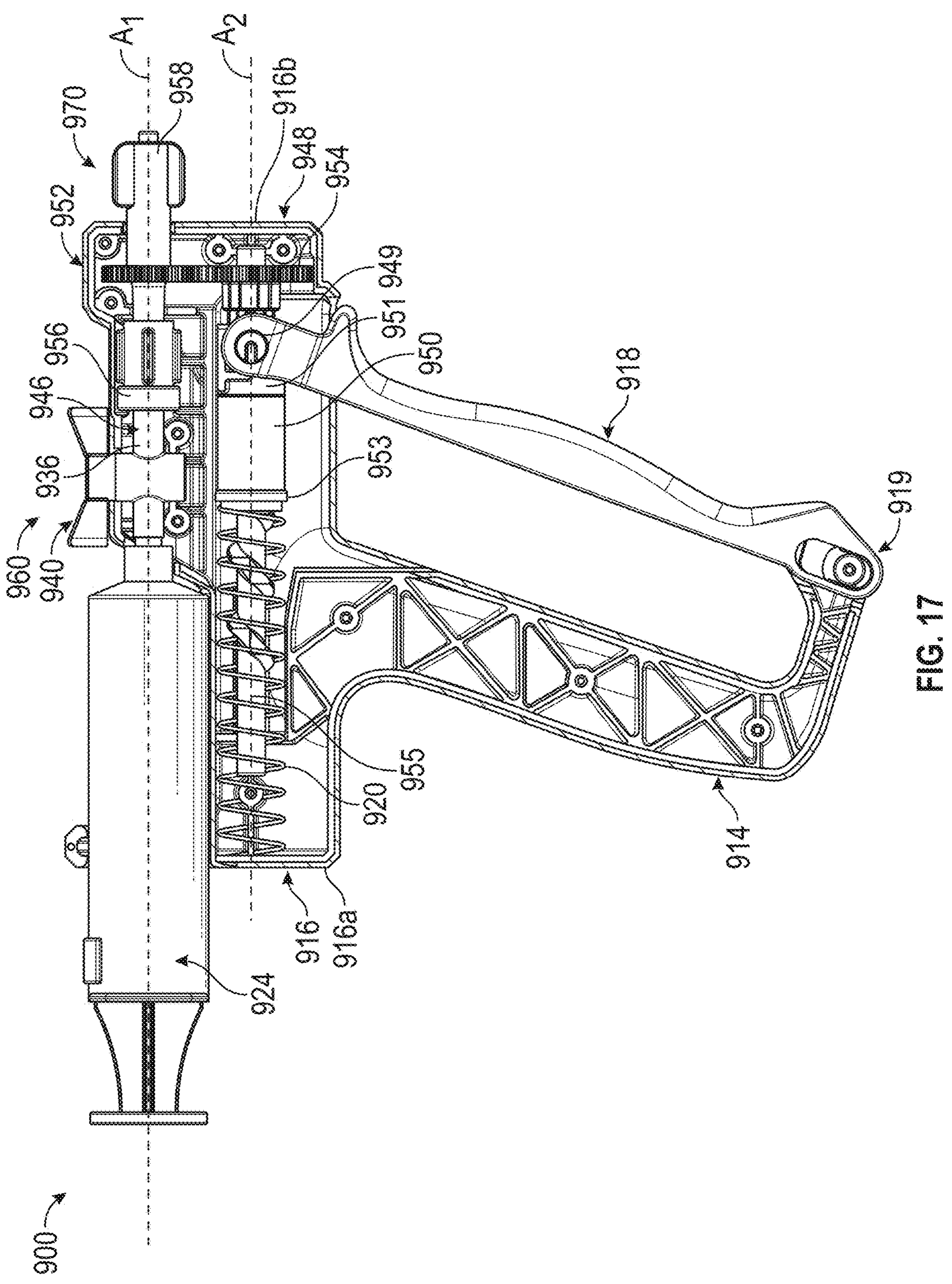
FIG. 17 shows a cross-sectional view of an exemplary device, according to an embodiment of the present disclosure.
Figure 18:
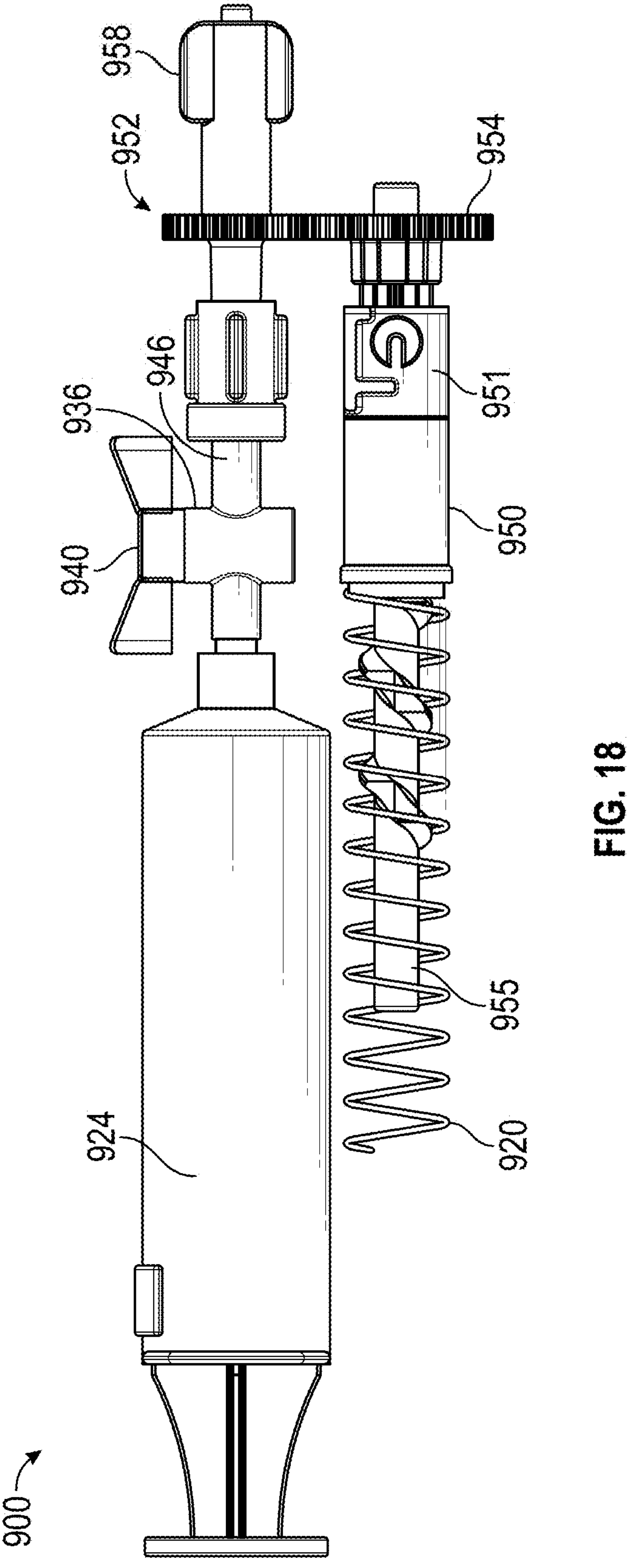
FIG. 18 shows a side view of the syringe and actuation device of FIG. 17, according to an embodiment of the present disclosure.

The exemplary device 900 of FIGS. 17 and 18 may be the same or similar as the device 10 and similar numerals are relied upon to describe like components. Components not described in FIGS. 17 and 18 may be the same or similar as to like illustrated components in device 10. The device 900 may be used in the aforementioned method. The device 900 may include a handle 914 and a trigger 918. The trigger 918 may include a pivot 919. The pivot 919 may be a pin or other fastener or device which allows for a pivoting action of the trigger 918. The pivot 919 may be a low pivot point. The pivot 919 may be located within the handle 914.

In this embodiment, the handle 914 includes the trigger 918 and a biasing member 920, in the form of a compression spring, such as a coil spring, although other biasing devices are contemplated. The biasing member 920 may begin in a neutral state to be compressed by the trigger 918 during actuation of the device 900. When force is released from the trigger 918, the compressed biasing member 920 may extend back to the neutral state.

The rotating component of the liquid flow path or lumen 946 of this embodiment is the gear/driver 952, which is separated from the valve 936 (e.g., a manual stop valve or non-rotating stopcock) and the plunger 924 (e.g., locking syringe) by a rotating seal 956. This rotating seal 956 is configured to provide a leak-free flow path along the lumen 946, while allowing free rotation between the ends of the device 900. The housing 916 supports and locates the components of the actuation system 948 or rotational drive mechanism and bearings/bushings may be added to reduce friction and ease rotation. The plunger 924, also referred to as a locking syringe 924, is non-rotating. The rotating seal 956 allows the proximal end of the valve 936, containing the valve, to remain stationary.

When the trigger 918 is actuated, it moves a free shuttle 951. The free shuttle 951 engages with and drives a drive shuttle 950, which features an internal helical pattern matching that of the helix 955. When the drive shuttle 950 passes over the helix 955, it causes the helix 955 to rotate about an axis $A_2$. This rotation spins the gear 954, which may be a helix gear 954, which drives the gear/driver 952 about an axis $A_1$, to which a catheter is connected (see, e.g., catheter 60 of FIGS. 2 and 5) via a coupling 958. The biasing member 920 (e.g., compression spring) returns the shuttles 950, 951 and the trigger 918 to their starting positions at the front of the device 900 (i.e., the right side of the device 900 in FIG. 17) after each trigger actuation. The axis $A_1$ and the axis $A_2$ are parallel. The slip ring 953 may reduce friction between the biasing member 920 and the drive shuttle 950. The teeth by which the drive shuttle 950 and the free shuttle 951 engage can be configured such that only rotation in one direction is allowed. According to one embodiment, it is advantageous to the function of the actuation system 948 or rotational drive mechanism that the catheter (e.g., catheter 60) rotate unidirectionally, so as the biasing member 920 (e.g., compression spring) returns the shuttles 950, 951 and the trigger 918 to their starting positions, the drive shuttle 950 will rotate freely around the helix 955 without engaging the free shuttle 951 or causing the helix 955 or gear/driver 952 to rotate. This motion may be repeated throughout the duration of the aspiration.

According to this embodiment, the aspiration process is simplified by the integration of a plunger 924 (e.g., locking syringe) and a valve 936 (e.g., stopcock). To create vacuum pressure, the valve 936 (e.g., stopcock) is set to a "closed" position, by depressing knob 940, and plunger 924 (e.g., locking syringe) is drawn. Rotation of the plunger 924 (e.g., locking syringe) allows it to lock in place, resisting the closing force created by the vacuum. The user may then proceed with other aspects of the procedure. For example, to remove emboli, the user will begin rotation with one hand via the trigger 918 and subsequently open the valve 936 (e.g., stopcock) with the other hand, using the knob 940, to release suction and begin aspiration of emboli. The aforementioned features of the embodiment of the device illustrated in FIGS. 17 and 18 allow for separation of the mechanisms of suction and rotation, while allowing for simultaneous suction and rotation, with the ability to begin rotation prior to suction, in order to agitate/disperse emboli prior to aspiration.

The components of the device 900 of FIGS. 17 and 18 are shown in more detail when referring to FIGS. 19 to 33.

Figure 19:
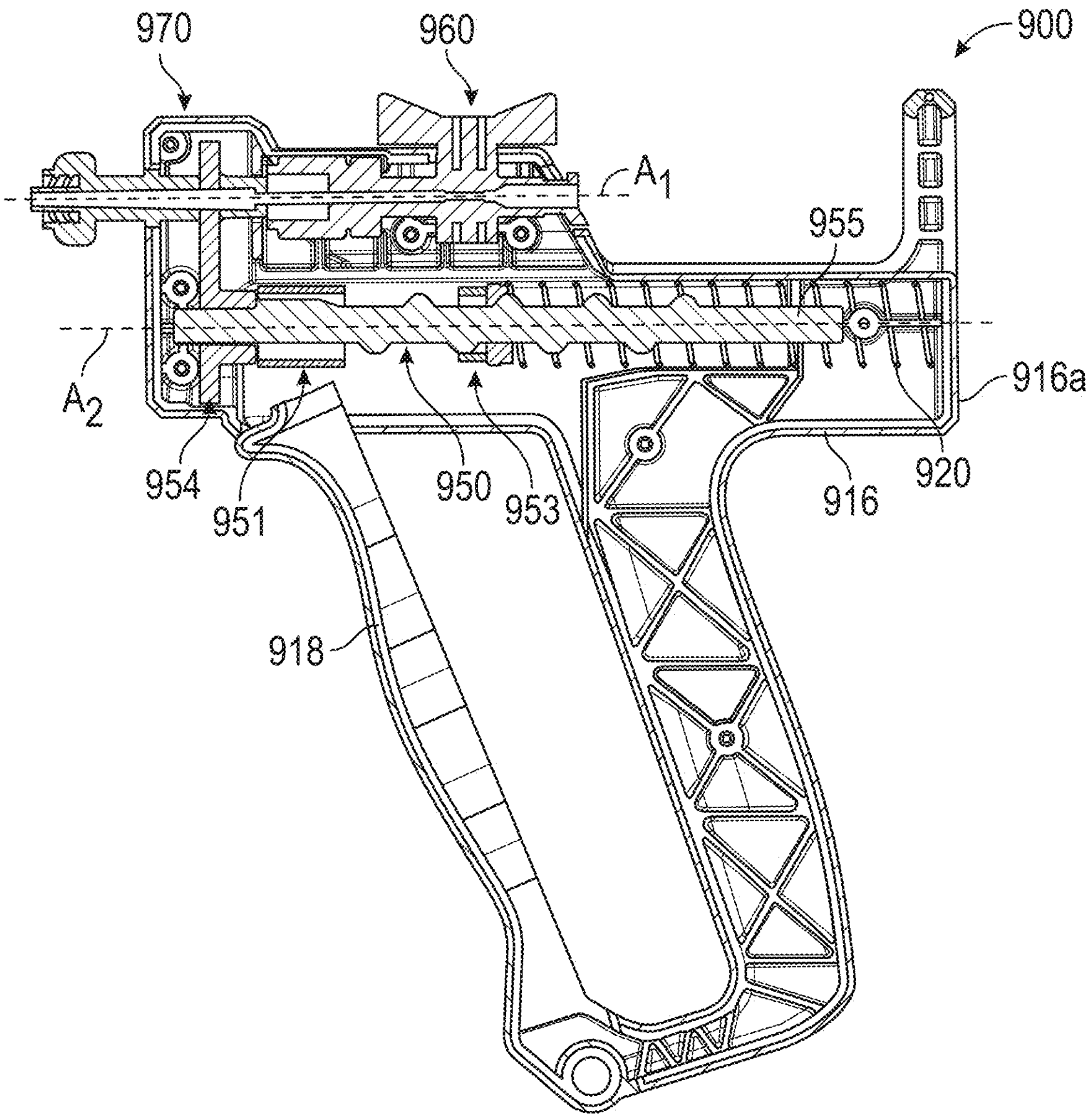
FIG. 19 shows a cross-sectional view of the device of FIG. 17, according to an embodiment of the present disclosure.
Figure 20:
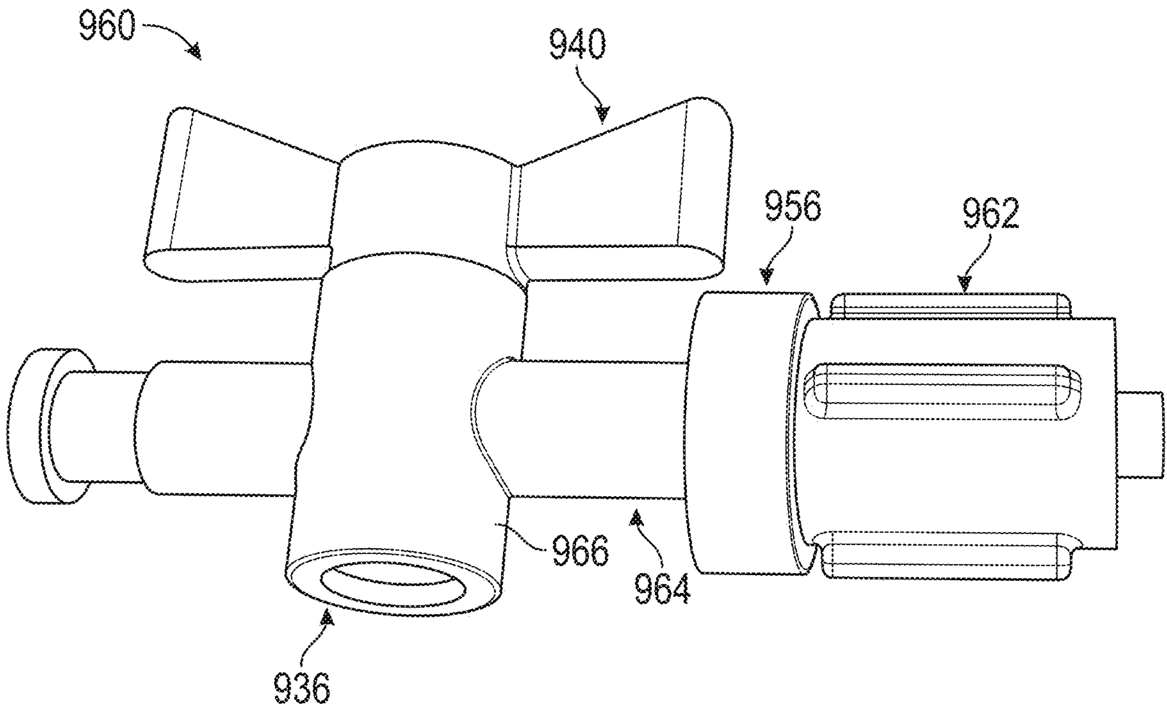
FIG. 20 shows a perspective view of a valve subassembly for the device of FIG. 17, according to an embodiment of the present disclosure.
Figure 21:
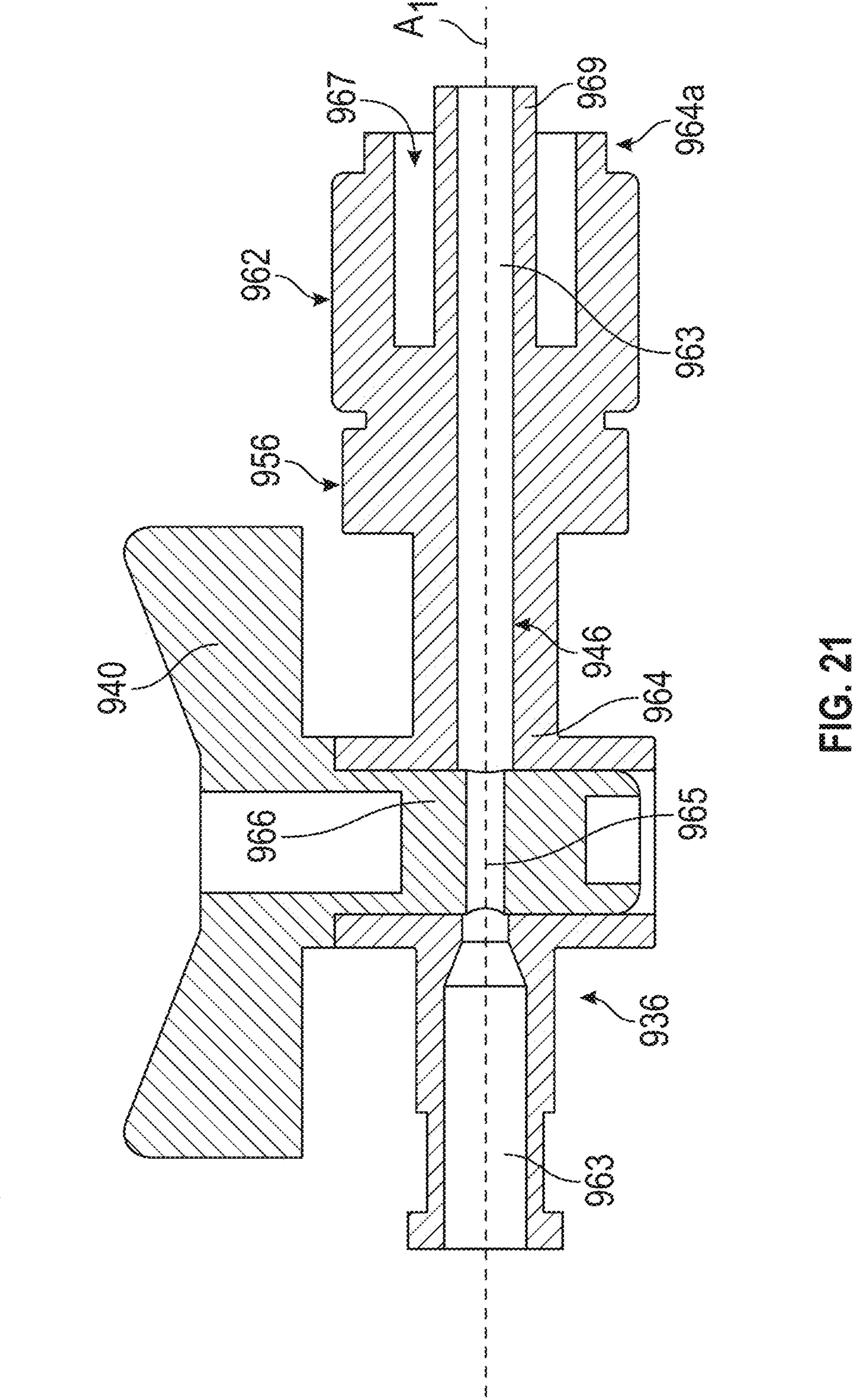
FIG. 21 shows a cross-sectional view of the valve subassembly of FIG. 20, according to an embodiment of the present disclosure.

Referring first to FIGS. 19 to 21, a valve subassembly 960 includes the valve 936, the knob 940, the rotating seal 956, and a portion of the lumen 946. As shown the portion of the lumen 946 that extends through the valve subassembly 960 includes a first portion 963 extending through a body 964 forming the valve subassembly 960 and a second portion 965 extending through a body 966 of the valve 936. As will be described in more detail, the first portion 963 fluidly connects to adjacent portions of the lumen 946 in adjacent components. During operation, the knob 940 is rotated to open and close the valve. For example, the knob 940 is rotated such that the second portion 965 rotates (from the view of FIG. 21) into a misaligned position with the first portion 963. In the rotated position, the body 966 blocks the flow from the catheter to the chamber of the plunger 924 (FIG. 18). In the position shown in FIG. 21, flow is permitted through the first portion 963 and the second portion 965 as the portions are in an aligned position allowing flow from the catheter to the chamber of the plunger 924 (FIG. 18). That is, the knob 940 is rotated in 90 degree increments to move the second portion 965 of the lumen 946 into and out of alignment with the first portion 963 of the lumen 946. For example, the knob 90 is turned 90 degrees into or out of the page (when viewing FIG. 21) and the orientation of the second portion 965 turns 90 degrees as well, resulting in a blockage of the lumen 946 by the body 966. Another 90 degree rotation realigns the first portion 963 and the second portion 965, allowing flow through the lumen 946. In some examples, the knob 940 is depressed to allow the selective opening and closing of the valve, In this example, the second portion 965 is moved downward out of alignment with the first portion 963. Although illustrated as component with two wings, the knob 940 may take other forms that allow for rotation or depression of the valve 936 to provide selective flow through the lumen 946.

With continued reference to FIGS. 19 to 21, and as described previously, the rotating seal 956 provides a leak-proof path through the lumen 946 while along for relative rotation between the rotation subassembly 970 (FIG. 22) and the valve subassembly 960. Thus, the body 964 of the valve subassembly 960 is stationary with respect to the housing 916 (FIG. 17).

Figure 22:
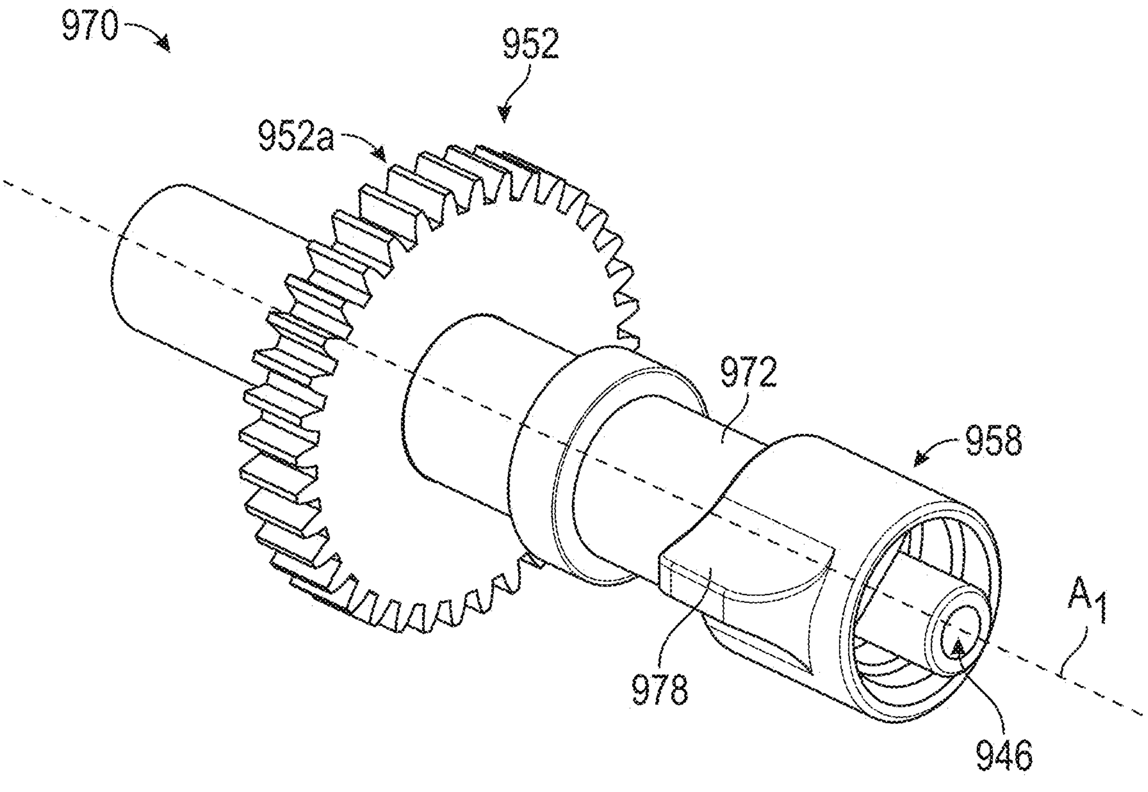
FIG. 22 shows a perspective view of a rotation subassembly for the device of FIG. 17, according to an embodiment of the present disclosure.
Figure 23:
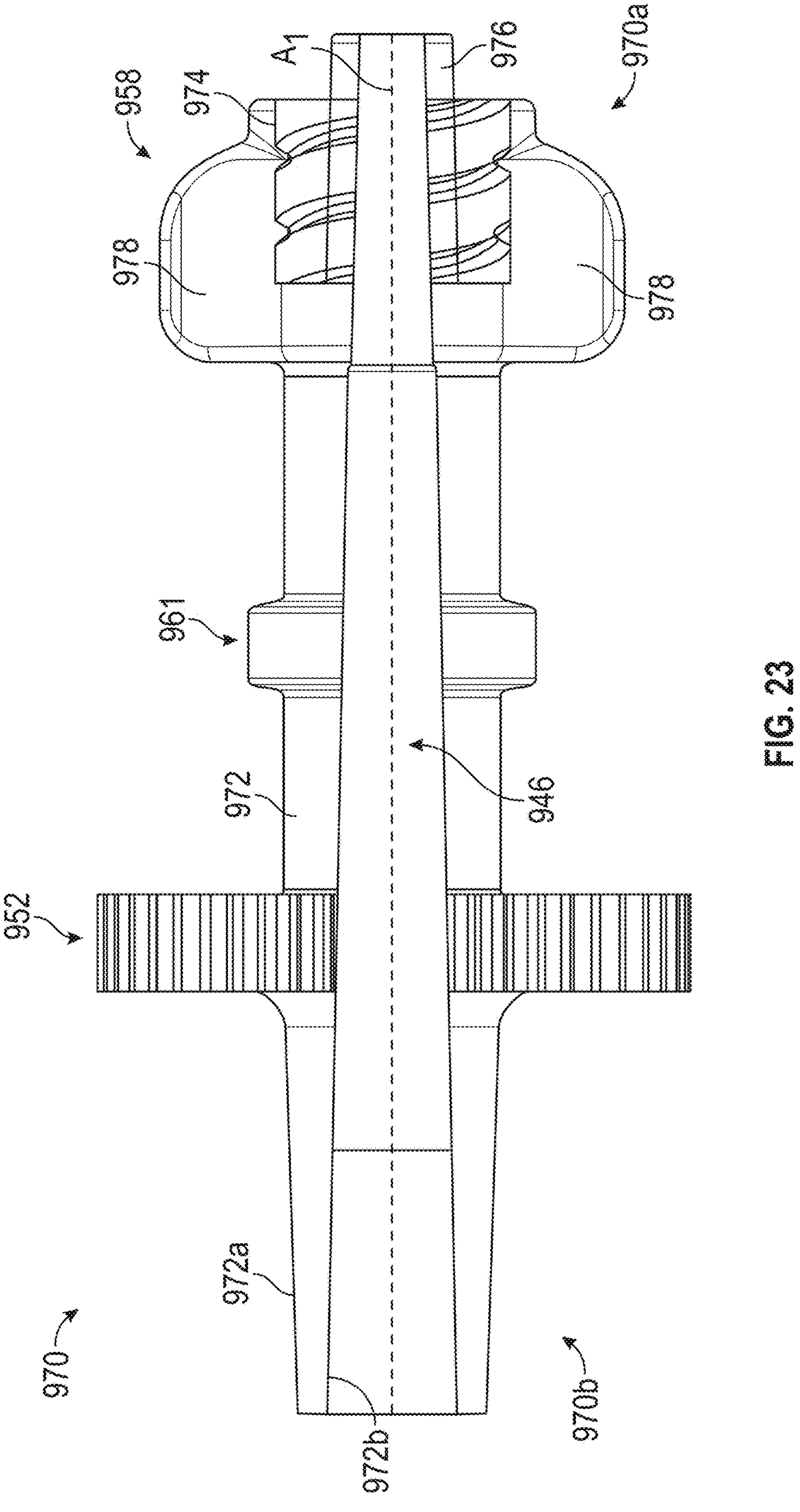
FIG. 23 shows a cross-sectional view of the rotation subassembly of FIG. 22, according to an embodiment of the present disclosure.

Referring now to FIGS. 19, 22, and 23, the rotation subassembly 970 includes the coupling 958 for coupling the lumen 946 to the catheter (not shown) and the gear 952. The rotation subassembly 970 has a single, integral, unitary, monolithic body 972. At a distal, first end 970*a* of the rotation subassembly 970 is the coupling 958. The coupling 958 includes an internal threaded surface 974, a protrusion 976, and one or more fins 978. The internal threaded surface 974 has a thread profile configured to mate with a corresponding thread profile on an outer surface of an end of the catheter. Thus, the catheter may be threadedly coupled to the rotation subassembly 970. With this connection, the catheter rotates in conjunction with rotation of the rotation subassembly 970. The protrusion 976 of the coupling 958 forms the inlet to the lumen 946. The protrusion 976 is received within the end of the catheter that couples to the internal threaded surface 974 to provide a continuous flow path form an interior of the catheter to the lumen 946. The rotation subassembly 970 includes a bearing surface 961. The bearing surface 961 extends radially outward from the outer surface 972*b*. The bearing surface 961 allows for a close concentricity between the rotation subassembly 970 and the housing 916 during relative rotation of the rotation subassembly 970 with respect to the housing 916. The bearing surface 961 may be integral with the body 972, as described above. Alternatively, the bearing surface 961 may be a bushing collar located around the outer surface 972*b* of the body 972. In some examples, the collar may be a nylon bushing collar.

The rotation subassembly 970 includes the gear 952, also referred to herein as a driver. As described previously, the gear 952 is caused to rotate by the gear 954 and causes rotation of the catheter (omitted for clarity). Since the gear 952 is formed integrally and unitarily with the body 972, rotation of the gear 952 causes rotation of the body 972, which is also formed integrally and unitarily with the coupling 958. Thus, the coupling 958 rotates with the gear 952. With the coupling 958 rotating, the catheter connected thereto also rotates, which, as described previously, results in rotation of the distal end of the catheter to facilitate removal of material within the vasculature. Although shown and described as a single, unitary part, the rotation subassembly 970 may be formed of multiple components coupled together with one or more attachment or connection devices.

Referring to FIGS. 19, 21, and 23, a proximal, second end 970*b* of the rotation subassembly 970 is connected to a first, distal end 964*a* (FIG. 21) of the valve subassembly 960. As shown in FIG. 21, the valve subassembly 960 includes an annular recess 967 formed between the body 964 and a protrusion 969. The second, proximal end 970*b* is received within the annular recess 967 such than an outer surface 972*a* of the body 972 and an inner surface 972*b* of the body 972 are located within the annular recess 967. That is, the inner surface 972*b* extends around the protrusion 969 and the body 964 of the valve subassembly 960 extends around the outer surface 972*a*. When the valve subassembly 960 and the rotation subassembly 970 are coupled together, as shown in FIGS. 17 to 19, the lumen 946 of FIG. 21 and the lumen 946 of FIG. 23 are aligned permitting flow from the catheter (omitted for clarity), through the rotation subassembly 970, through the valve subassembly 960, and into the chamber of the plunger 924.

As mentioned previously, the valve subassembly 960 does not rotate with respect to the axis $A_1$ and the rotation subassembly 970 does rotate with respect to $A_1$. Thus, although the second end 970*b* is received within the first end 964*a*, relative rotation between the body 972 and the body 964 is permitted. The rotating seal 956 prevents leakage between the body 972 and the body 964. Together, the rotation subassembly 970, the valve subassembly 960, and the plunger 924 form a suction path having a central axis that coincides with the axis $A_1$.

FIGS. 24 to 33 illustrate the various features of the actuation system 948. As described herein, the actuation system 948 includes the rotation subassembly 970, the gear 954, the free shuttle 951, the drive shuttle 950, the slip ring 953, the helix 955, and the biasing member 920. Together, the actuation system forms a drive path having a central axis that coincides with the axis $A_2$. A central axis of each of the gear 954, the free shuttle 951, the drive shuttle 950, the slip ring 953, the helix 955, and the biasing member 920 all coincide with the axis $A_2$.

Figure 24:
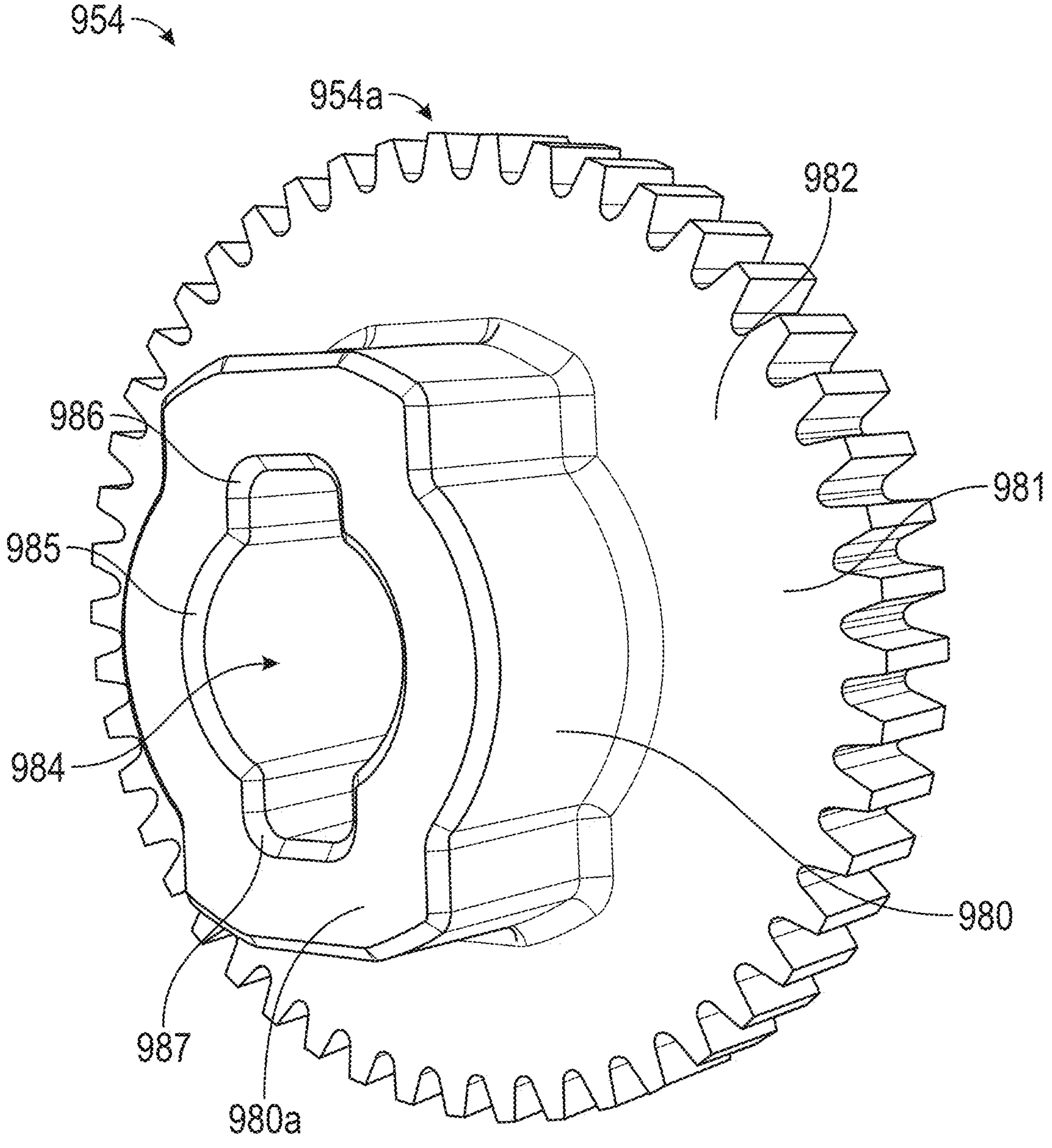
FIG. 24 shows a perspective view of a gear for the device of FIG. 17, according to an embodiment of the present disclosure.
Figure 25:
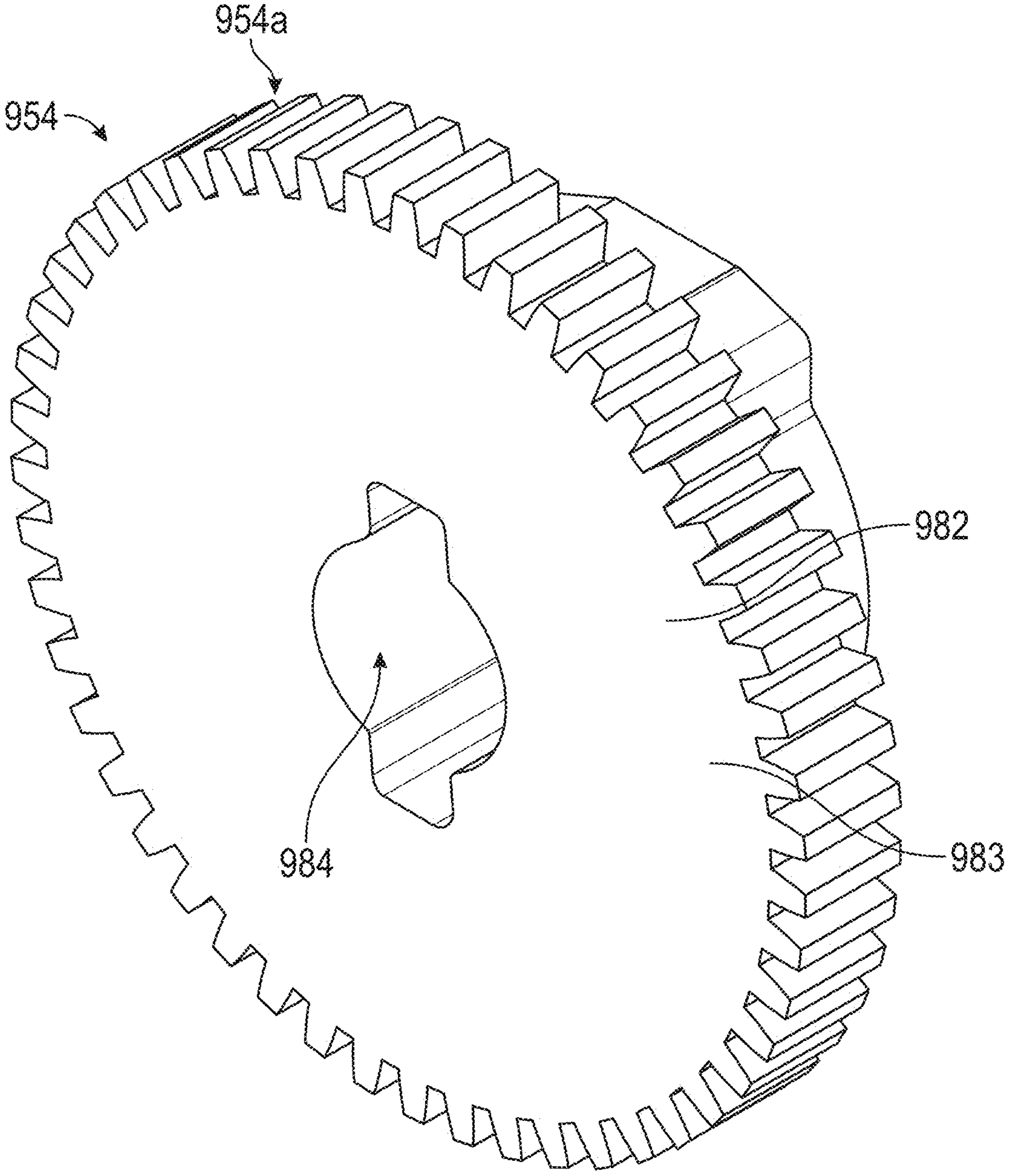
FIG. 25 shows another perspective view of the gear of FIG. 24, according to an embodiment of the present disclosure.
Figure 33:
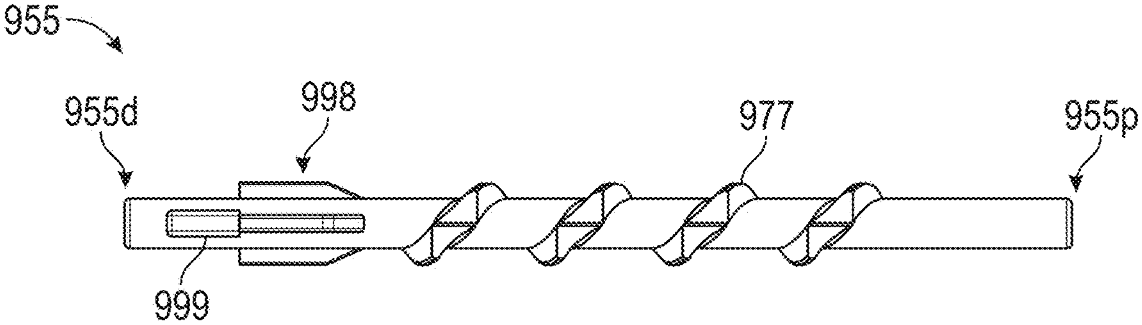
FIG. 33 shows a side view of the helix of FIG. 32, rotated 90 degrees, according to an embodiment of the present disclosure.
Figure 34:
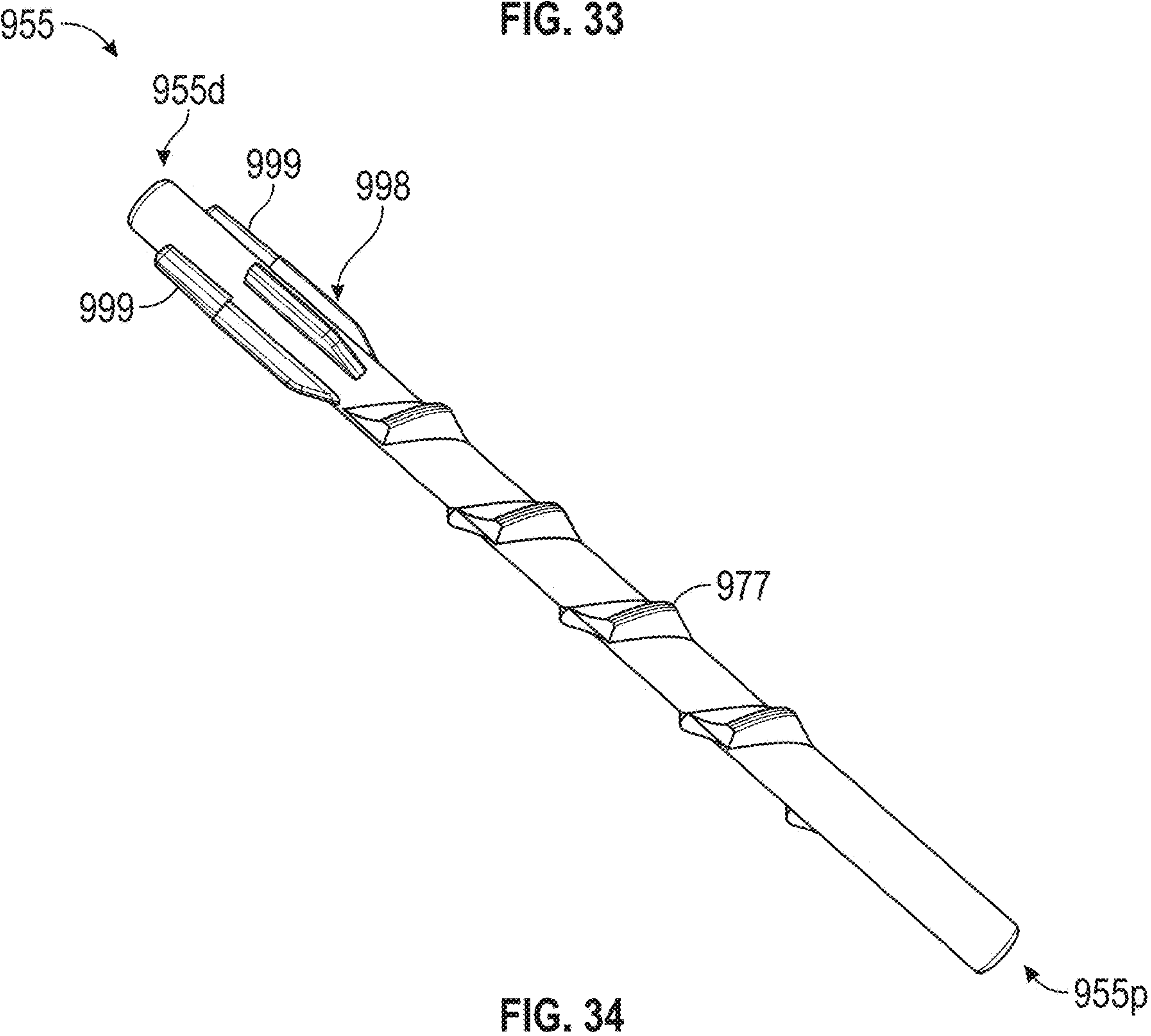
FIG. 34 shows a perspective view of the helix of FIG. 32, according to an embodiment of the present disclosure.

FIGS. 24 and 25 illustrate the gear 954. The gear 954 has teeth 954*a* that mesh with teeth 952*a* (FIG. 22) of the gear 952. Accordingly, when gear 954 is caused to rotate by the trigger 918 (FIG. 17), the meshing gear teeth cause the gear 952 to rotate (which, as described above, causes rotation of the catheter). The gear 954 includes a protrusion 980 extending from a first side 981 of a body 982 of the gear 954. A second side 983 of the body 982 is flat and planar to allow for mating and/or touching of the adjacent free shuttle 951. The protrusion 980 includes an opening 984 that extends fully through the protrusion 980 and through the body 982. The helix 955 (FIG. 19) extends through the opening 984. The opening 984 includes a circular portion 985, a first lobe 986, and a second lobe 987. The first lobe 986 and the second lobe 987 are sized and shaped to mate with protrusions 999 of the helix 955 (FIG. 33). When assembled, the protrusions 99 are received within the first lobe 986 and the second lobe 987, respectively. This engagement allows for co-rotation of the helix 955 and the gear 954. That is, when the helix 955 rotates, the mating engagement of the lobes and the protrusions causes the gear 954 to rotate, which, in turn causes the gear 952 to rotate and thus, causes the catheter to rotate. FIG. 19 illustrates the helix 955 extending past the second side 983 of the gear 954. However, the helix 955 need not extend past, so long as the protrusions are located within the lobes, as previously described.

Figure 26:
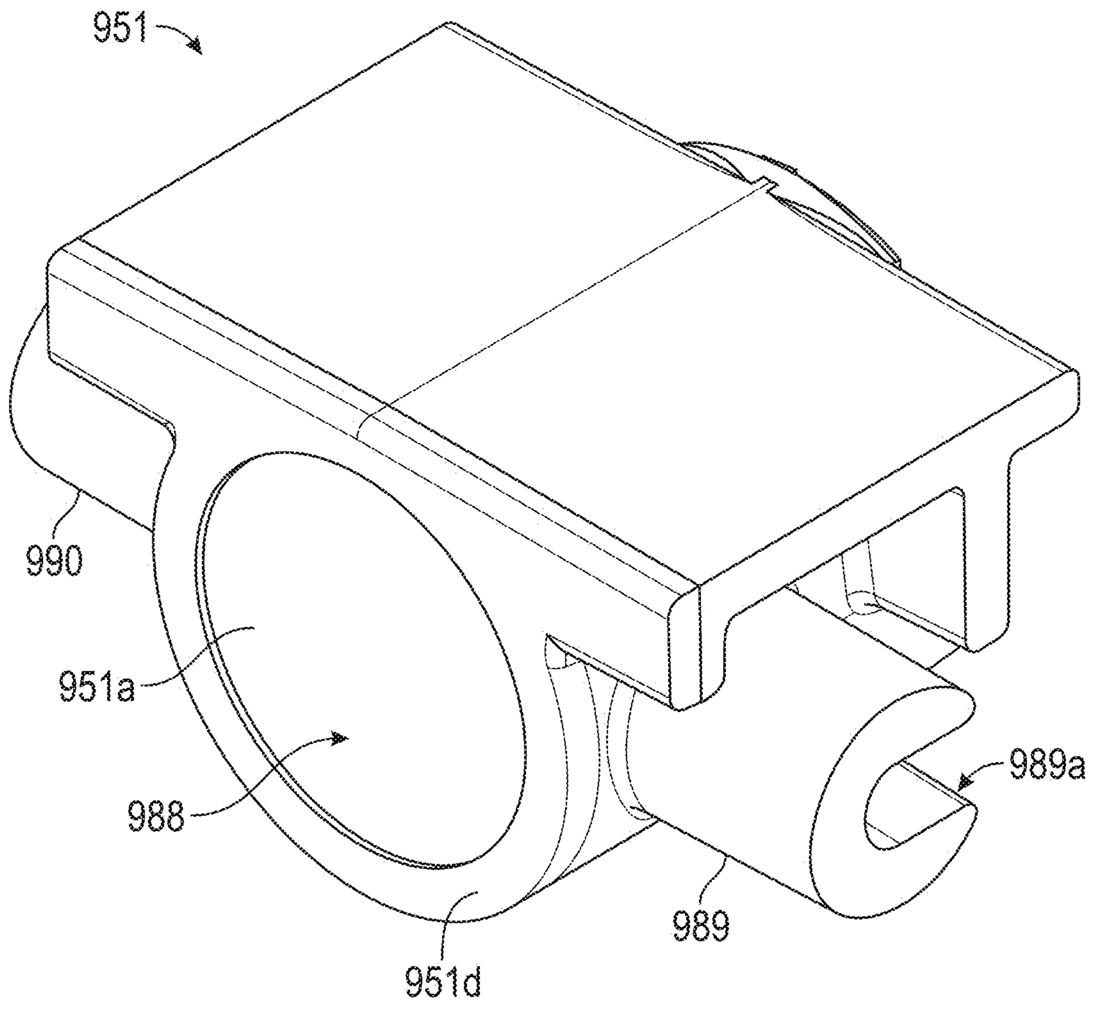
FIG. 26 shows a perspective view of a free shuttle for the device of FIG. 17, according to an embodiment of the present disclosure.
Figure 27:
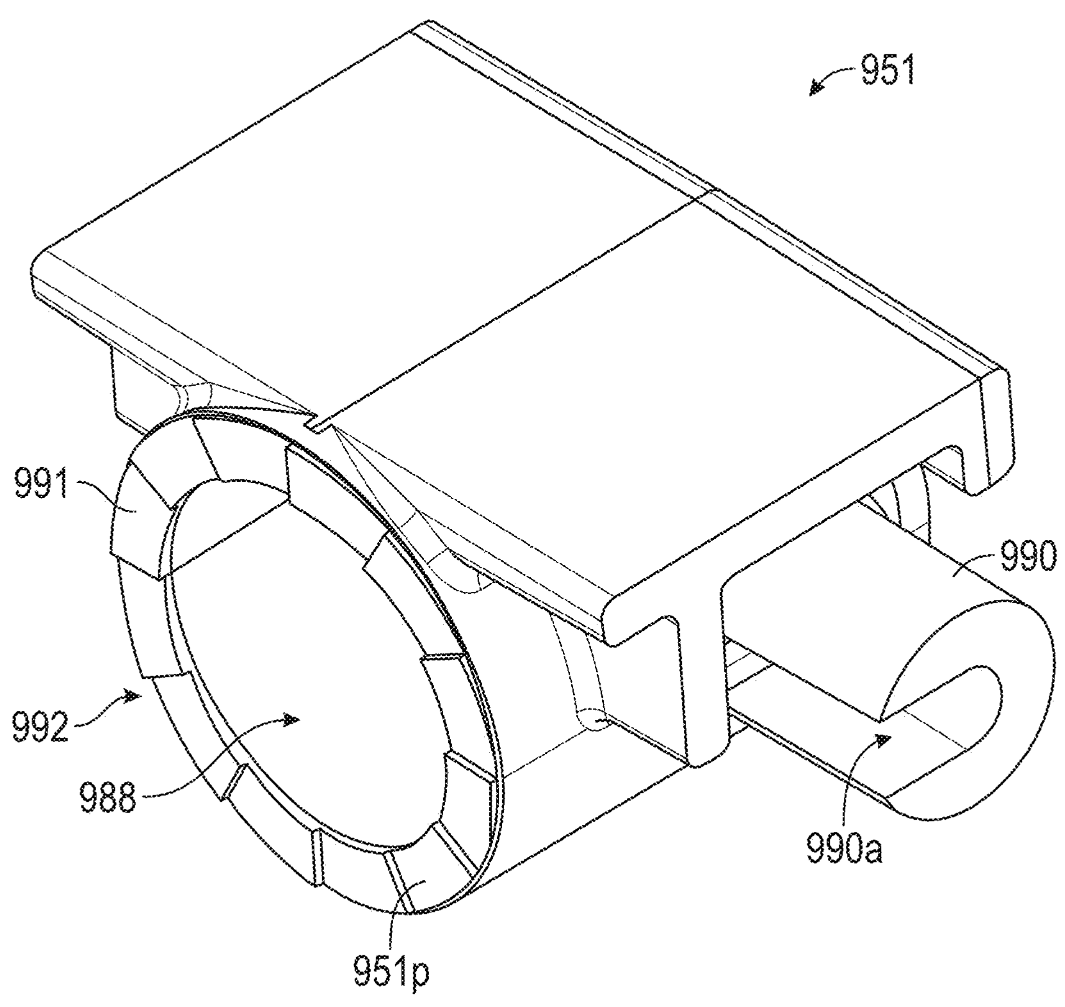
FIG. 27 shows another perspective view of the free shuttle of FIG. 26, according to an embodiment of the present disclosure.

FIGS. 26 and 27 illustrate the free shuttle 951. The free shuttle 951 has an opening 988. When assembled, the helix 955 extends through the opening 988. An inner surface 951*a* of the free shuttle 951 is unadorned and has no surface features. That is, the inner surface 951*a* is substantially smooth. Thus, the helix 955 rotates freely within the free shuttle 951 without causes the free shuttle 951 to rotate. The free shuttle 951 also includes a first protrusion 989 and a second protrusion 990. The first protrusion 989 and the second protrusion 990 may be the same or similar. The first protrusion 989 has a first protrusion opening 989*a* and the second protrusion 990 has a second protrusion opening 990*a*. Referring briefly to FIG. 17, the trigger 918 includes an opening 949 on opposing sides of the trigger 918. That is, a similar opening to the opening 949 is located on the other side of the device not visible in FIG. 17. Referring to FIGS. 17, 26, and 27, the openings 949 each receive the first protrusion 989 and the second protrusion 990, respectively.

Accordingly, due to the interaction of the protrusions and openings, depression of the trigger 918 by the user causes longitudinal movement of the free shuttle 951 toward a proximal end 916*a* of the housing 916.

Referring again to FIGS. 26 and 27, a distal end 951*d* of the free shuttle 951 is adjacent and end 980*a* (FIG. 24) of the gear 954. A proximal end 951*p* includes a plurality of steps 991. The steps 991 form a ratchet profile 992. The ratchet profile 992 is formed such that rotation of the drive shuttle 950 (FIG. 19) with respect to the free shuttle 951 is permitted in only one direction. That is, as the free shuttle 951 and the drive shuttle 950 move longitudinally toward the proximal end 916*a* of the housing 916, relative rotation between the free shuttle 951 and the drive shuttle 950 is prohibited. Thus, no rotation of either the free shuttle 951 or the drive shuttle 950 is permitted when the trigger 918 is depressed or actuated. After the trigger is released and the biasing member 920 moves the actuation system 948 back to the initial position, the drive shuttle 950 is allowed to rotate along the helix 955 to the starting position of the drive shuttle 950 nearer to the distal end 916*b* of the housing 916. As the drive shuttle 950 rotates and moves longitudinally toward the distal end 916*b*, the ratchet profile 994 (FIG. 28) on the drive shuttle 950 moves along the ratchet profile 992 of the free shuttle 951. Thus, the drive shuttle 950 moves longitudinally and rotationally back toward the distal end 916*b* and the free shuttle 951 moves longitudinally, but does not rotate, back toward the proximal end 916*a*.

Figure 28:
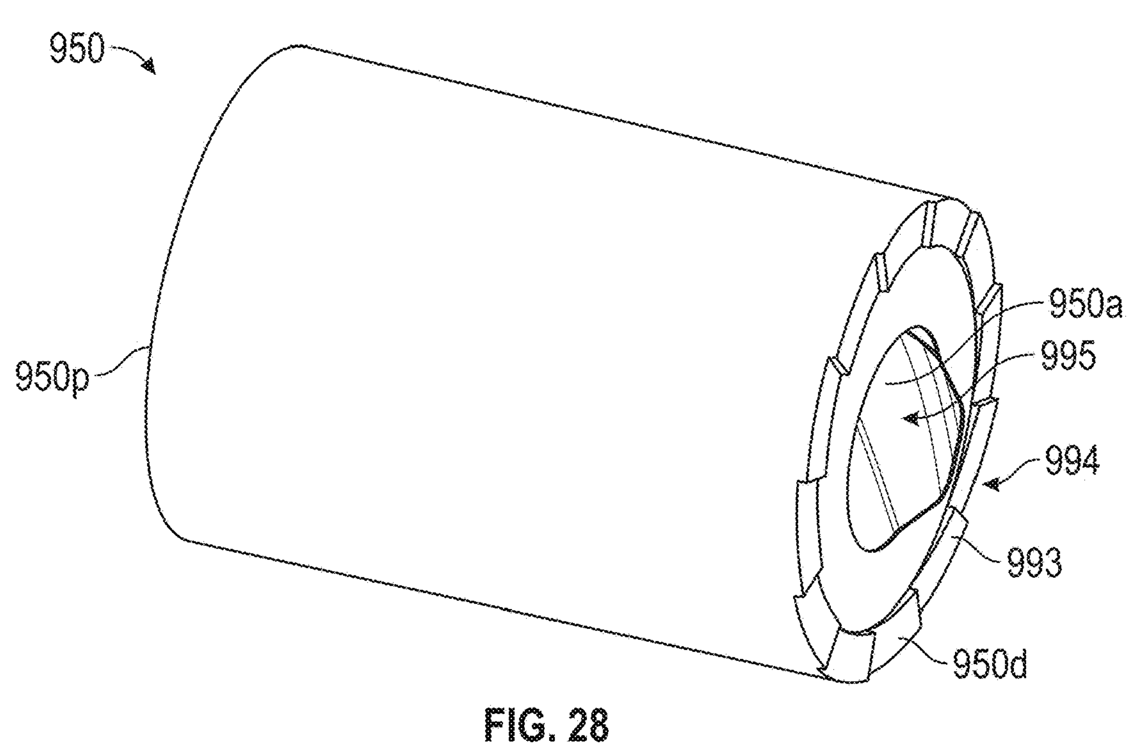
FIG. 28 shows a perspective view of a drive shuttle for the device of FIG. 17, according to an embodiment of the present disclosure.
Figure 29:
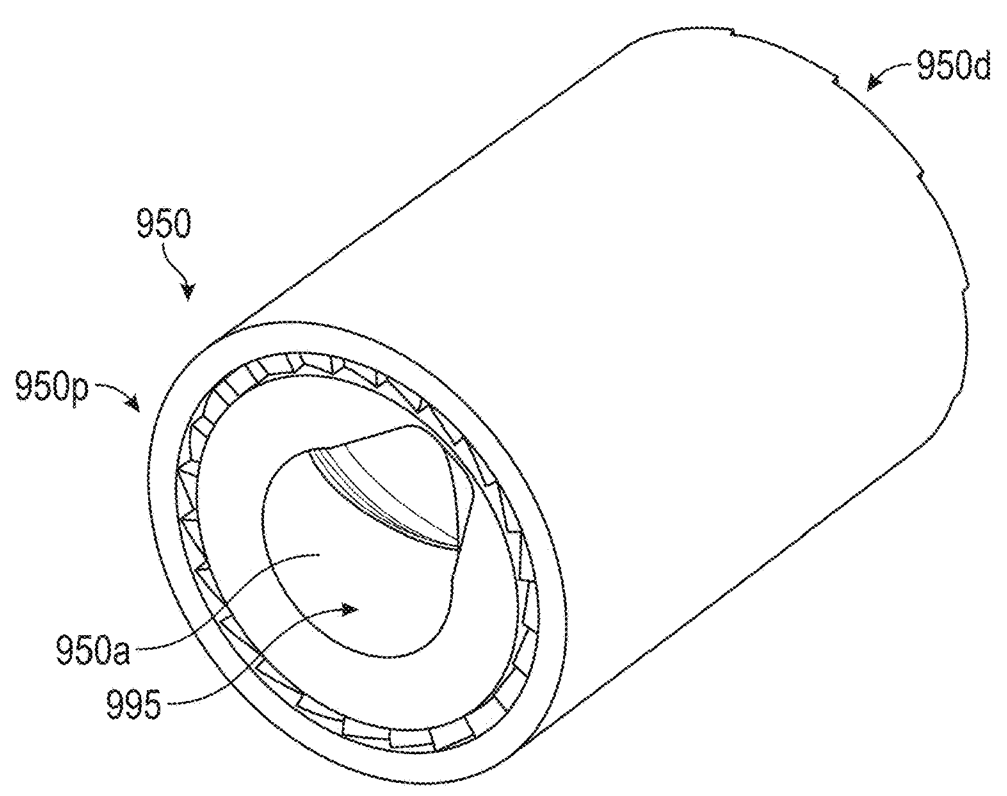
FIG. 29 shows another perspective view of the drive shuttle of FIG. 28, according to an embodiment of the present disclosure.
Figure 30:
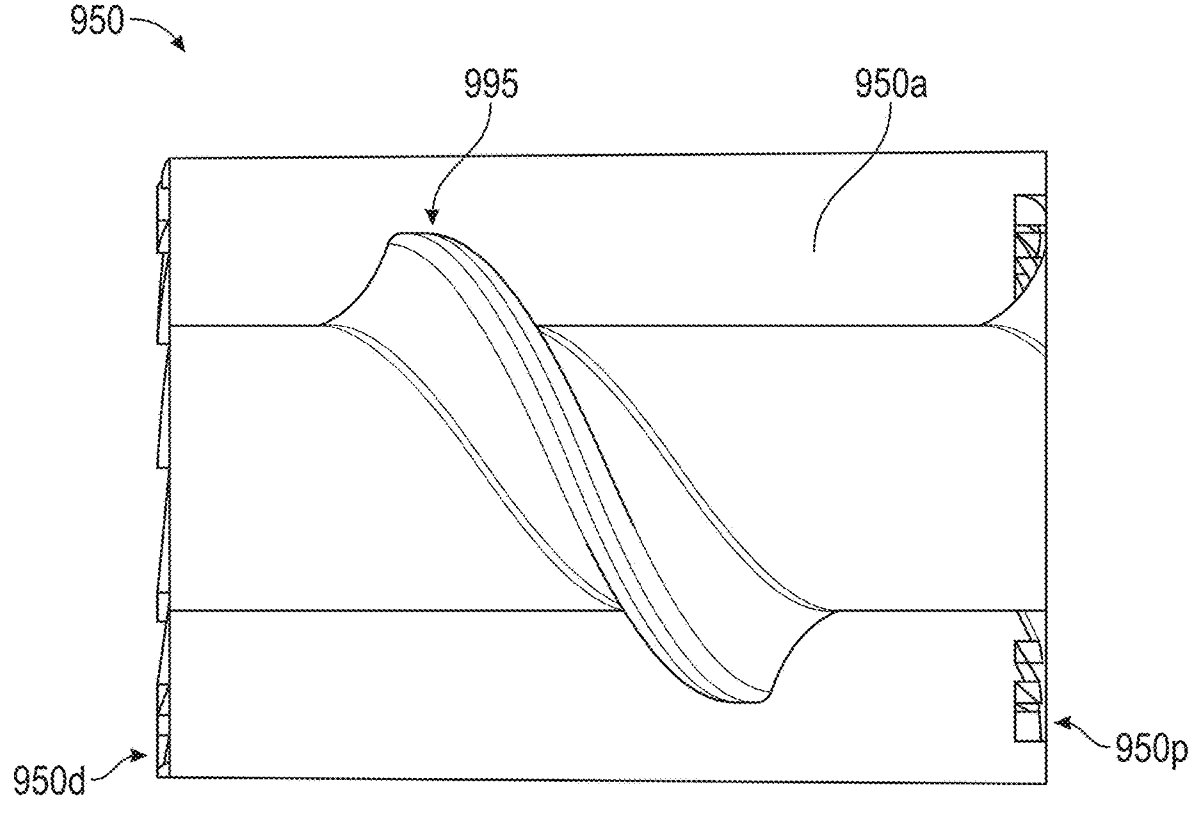
FIG. 30 shows a cross-sectional view of the drive shuttle of FIG. 28, according to an embodiment of the present disclosure.

FIGS. 28 to 30 illustrate the drive shuttle 950. The drive shuttle 950 has a proximal end 950*p* and a distal end 950*d*. The proximal end 950*p* includes a plurality of steps 993. The steps 993 form a ratchet profile 994. The ratchet profile 994 is formed such that rotation of the drive shuttle 950 with respect to the free shuttle (FIG. 19) is permitted in only one direction. The permitted rotational direction is opposite of the direction of rotation of the catheter. Thus, when rotation of the catheter is clockwise, the drive shuttle permitted to rotate counterclockwise, and vice versa. The interaction of the ratchet profile 994 and the ratchet profile 992 is as described with respect to FIGS. 26 and 27. The proximal end 950*p* is adjacent to and may touch the slip ring 953 (FIG. 19).

As shown in FIG. 30, the drive shuttle 950 includes an internal helix profile 995 on an internal surface 950*a* of the drive shuttle 950. As described herein, the internal helix profile 995 mates with an external helix profile 997 of the helix 955 to cause rotation of the helix 955. That is, since the drive shuttle 950 is prevented from rotation during actuation of the device (e.g., during depression of the trigger 918), the longitudinal movement of the drive shuttle 950 toward the proximal end 916*a* of the housing 916 causes the external helix profile 997 of the helix 955 to move along the internal helix profile 995 causing rotation of the helix 955 with respect to the drive shuttle 950 (which is not rotating during actuation).

Figure 31:
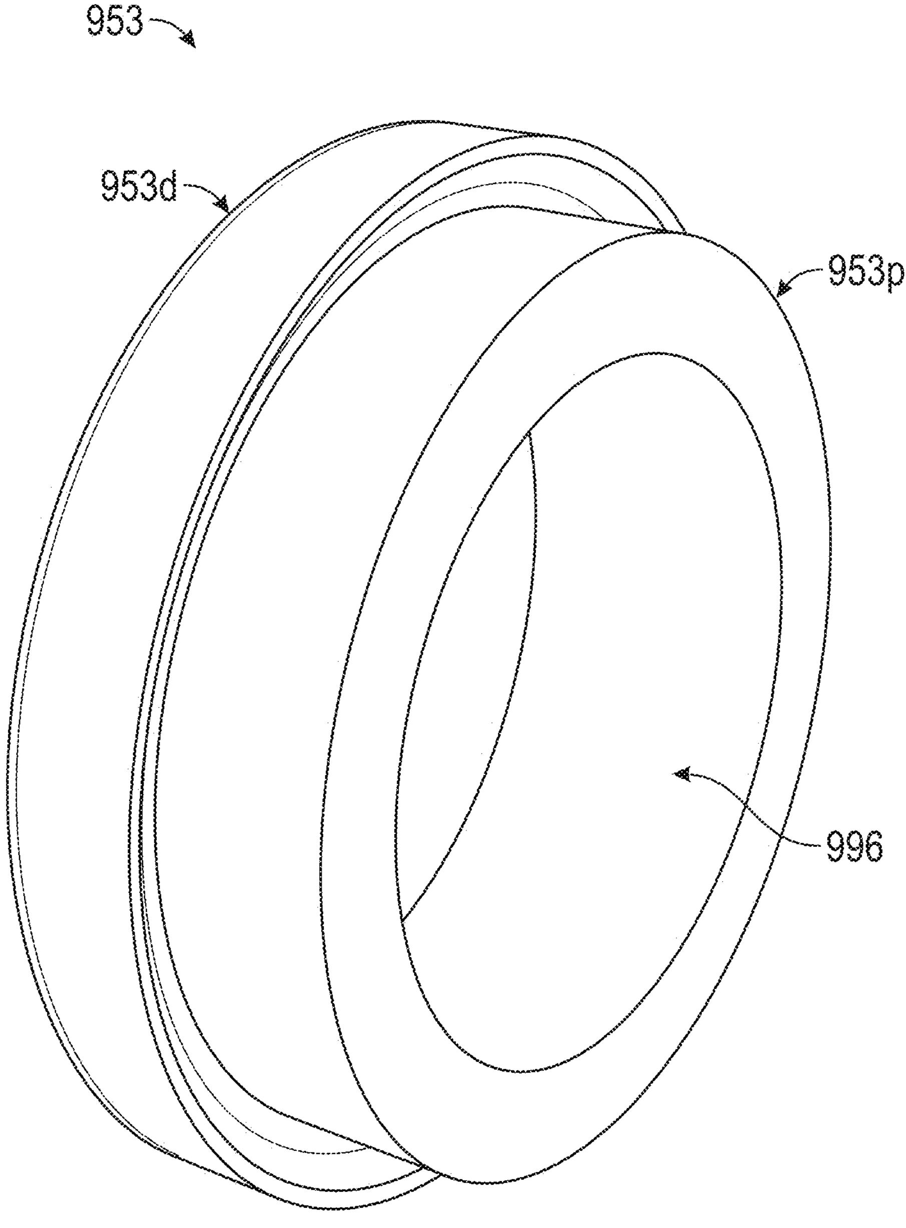
FIG. 31 shows a perspective view of a slip ring for the device of FIG. 17, according to an embodiment of the present disclosure.
Figure 32:
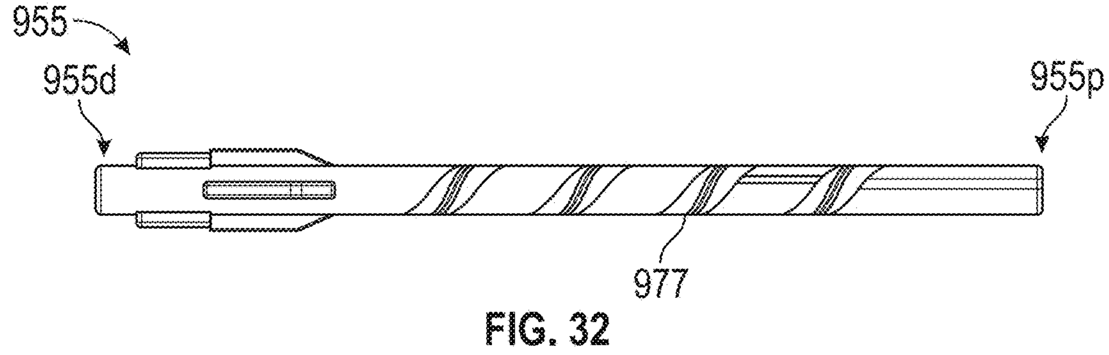
FIG. 32 shows a side view of a helix for the device of FIG. 17, according to an embodiment of the present disclosure.

FIG. 31 illustrates the slip ring 953. The slip ring 953 has a proximal end 953*p* and a distal end 953*d*. The distal end 953*d* is adjacent to and may touch the proximal end 950*p* of the drive shuttle 950. The slip ring 953 has an opening 996 that receives the helix 955. The opening 996 is large enough to receive the helix 955 and the external helix profile 997 without interacting with either the helix 955 or the external helix profile 997. The slip ring 953 may reduce friction between the biasing member 920 and the drive shuttle 950 (FIG. 19).

FIGS. 31 to 34 illustrate the helix 955. The helix 955 has a proximal end 955*p* and a distal end 955*d*. The distal end 955*d* may be located near the distal end 916*b* of the housing 916. The helix 955 includes an external helix profile 997 that extends along a portion of the helix 955. The external helix profile 977 and the internal helix profile 995 (FIG. 30) are shaped and sized to conform or mate with one another such that relative rotation of one part (either the helix 955 or the drive shuttle 950) is permitted with respect to the other part (the other of the helix 955 or the drive shuttle 950). During operation, as will be described in more detail to follow, the helix 955 causes rotation of the gear 954, which in turn, causes rotation of the gear 952 and the catheter. The helix 955 includes a plurality of first protrusions 998. When assembled, the protrusions 998 are located within the opening 988 of the free shuttle 951. The protrusions 998 provide axial alignment between the free shuttle 951 and the drive axis $A_2$. That is, the protrusions 998 maintain the free shuttle 951 centered over the drive axis $A_2$. The helix 955 includes a plurality of second protrusions 999. As shown, there may be two second protrusions 999 to correspond to the two lobes 986, 987 of the gear 954 (FIG. 24), though more or fewer are contemplated. As discussed previously, the interaction of the protrusions 999 and the lobes 986, 987 allows for rotation of the helix 955 to be transferred to the gear 954 to allow for rotation of the gear 954, and, in turn, the catheter.

As shown in FIGS. 17 and 19, the helix 955 extends through the slip ring 953, the biasing member 920, the free shuttle 951, the drive shuttle 950, and the gear 954. During operation, the helix 955 is allowed to rotate freely relative to the free shuttle 951. With respect to the gear 954 and the drive shuttle 950, the helix 955 has interacting features and rotation of the drive shuttle 950 causes rotation of the helix 955 (due to the mating helix surfaces), which in turn causes rotation of the gear 954 (due to the protrusion and lobe interaction).

Accordingly, during operation, as described with respect to FIGS. 17 and 19, when the trigger 918 is depressed, the free shuttle 951 is caused to move longitudinally along the axis $A_2$ and along the helix 955 toward a proximal end 916*a* of the housing 916. The longitudinal movement of the free shuttle 951 causes the end surface of the free shuttle to interact with the end surface of the drive shuttle 950, thus causing the free shuttle to move longitudinally along the axis $A_2$ and along the helix 955 toward the proximal end 916*a* of the housing 916. Due to the mating ratchet profiles 992, 994, relative rotation is prohibited and neither the free shuttle 951 nor the drive shuttle 950 rotate during the activation (e.g., when the trigger is depressed) of the device 900. Due to the mating helix surfaces 997, 995 of the helix 955 and the drive shuttle 950, respectively, the longitudinal movement of the drive shuttle 950 causes rotation of the helix 955. That is, since the drive shuttle 950 does not rotate, the helix is forced to rotate as the external helix profile 997 of the helix 955 follows along the internal helix profile 995 of the drive shuttle 950. The rotation of the helix 955 then causes rotation of the gear 954 (due to the protrusion and lobe interaction described with respect to FIGS. 24 and 25). Rotation of the gear 954 causes rotation of the gear 952 (due to the meshing teeth) and the rotation of the gear 952, being coupled to the catheter, causes rotation of the catheter. As may be appreciated from the foregoing disclosure, the linear motion of the trigger 918 is thus translated into the rotational motion of the catheter by the actuation system 948.

When the trigger 918 is released, the device 900 is automatically returned to the starting condition. The biasing member 920 is compressed during the aforementioned actuation of the device 900. When the trigger 918 is released, the biasing member 920 expends its stored energy to push the slip ring 953 toward the distal end 916*b* of the housing. As the biasing member 920 pushes the slip ring 953, the end of the slip ring 953 pushes the drive shuttle 950 toward the distal end 916*b*. The internal helix profile 995 travels along the helix profile and the drive shuttle 950 rotates along the helix 955 as the drive shuttle 950 moves toward the distal end 916*b*. The end of the drive shuttle 950 ratchets along the ratchet profile and longitudinally pushes the free shuttle 951 toward the starting position.

Accordingly, as understood from the foregoing disclosure, the free shuttle 951 does not rotate either in the actuation or returning conditions, the free shuttle 951 is only allowed to move longitudinally along the axis $A_2$ (in both directions). The drive shuttle 950 is allowed to move longitudinally along the axis $A_2$ (in both directions), but is not permitted to rotate during actuation and is permitted to rotate during return. The helix 955 does not move longitudinally and only rotates about the axis $A_2$.

The device of the present disclosure may allow for the removal of material from a remote location in the vasculature. The combination of the suction and rotation of the device may enhance the ability to remove material resulting in clearer vasculatures as compared to prior art devices. In an example of such a remote location, the device may be used in the artery of a lower extremity (e.g., a leg) in combination with an external cuff. The external cuff may create a dam preventing material from flowing throughout the body. With the external cuff in place, the device of the present disclosure may be utilized to fully clear any material from the vasculature at the location of the distal tip of the catheter of the device and/or at the location of an interventional procedure.

The device of the present disclosure may be used in conjunction with a blood pressure cuff placed distal to the vasculature being treated to stop the blood flow from going distal in the vasculature. A clot, thrombus, and distal emboli that can flow distally can cause additional problems if left in the vasculature. By placing the cuff distally, such additional problems may be avoided. The device may remove the material (e.g., clot, thrombus, emboli, or debris) therefrom.

As described herein, the device may remove material from within a vasculature. The material may be, but is not limited to, a clot, thrombus, emboli, obstruction, particles, fluid, plaque, debris, debris from an interventional procedure, or other material located in a vasculature. Although described in conjunction with an interventional procedure, the device itself may be used to perform the interventional procedure. That is, in one example, an interventional procedure may dislodge or destroy an obstruction in the vasculature and the device of the present disclosure may be employed to remove the debris caused by the interventional procedure. In another example, the device itself may dislodge or destroy the obstruction in the vasculature and may be subsequently, or simultaneously, remove debris caused by the dislodging or destruction.

The device of the present disclosure may comprise three core elements: a catheter, a proximal rotating element, and a negative pressure element. The catheter may be a braided, over-the-wire catheter with about a 4 French inner diameter and a 5 French outer diameter. The catheter may include a PTFE lined core and a tapered tip. The catheter may be 6 French guiding sheath compatible. The catheter may be sterile. The proximal rotating element may be secured to the catheter via a catheter hub. The proximal rotating element may be a mechanical tool which imparts rotational energy to the catheter. The proximal rotating element may include a central lumen to connect to the catheter distally and the negative pressure element proximally. The proximal rotating element may be sterile. The negative pressure element may be a simple, large capacity locking syringe with a two-way stop-cock or one of the devices described herein. The negative pressure element may be securely attached to the proximal rotating element. The negative pressure element may be sterile.

In an example method, upon removing from the sterile pouch and assembling the catheter and proximal rotating element, the device may be primed with heparinized saline. The device may be introduced over a compatible guidewire (for example, 0.014", 0.018" or 0.035") into the peripheral vasculature through a 6F sheath. The catheter may be delivered over the guidewire to the distal portion of the treated area. The delivery guidewire may be removed. The negative pressure element may be prepared by attaching the stopcock in the closed position. The plunger may be pulled back fully and locked to generate the full capacity of negative pressure. The negative pressure element may be attached to a proximal end of the proximal rotating element. The proximal rotating element may be engaged to impart rotational energy to the catheter and the stopcock may be opened to impart suction at the distal tip of the catheter to loosen and remove material, such as, for example, a thrombus and/or distal emboli. Upon reaching full capacity of the negative pressure element, the syringe (e.g., the device of the present disclosure) may be removed from the treatment zone and the contents may be emptied into a 30-50 μm filter. The process may be repeated prior as necessary prior to removing the system from the guiding sheath.

The cuff may be put on the patient any time prior to the intervention (e.g., work on the diseased artery is started). The cuff may be put on the patient when the patient is first prepared for the procedure. The cuff may be inflated prior to the intervention to stop blood flow prior to and during the intervention to keep thrombus, clot, or debris from flowing past the diseased area/cuff and removed by the device of the present disclosure. The cuff may then be deflated after the procedure and/or after an angiogram that confirms the positive results of the intervention and removal of the material via the device. If more interventional work is needed the cuff may be re-inflated to repeat the procedure as needed to fully remove the material from the vasculature.

According to an embodiment, a device for removing material from a vasculature may include a catheter having a lumen, a proximal end, and a distal tip; a proximal rotating element coupled to the proximal end of the catheter, the proximal rotating element configured to rotate the catheter; and a negative pressure element configured to create a controlled suction within a chamber of the device to remove the material from the vasculature, wherein the distal tip of the catheter rotates to assist in removal of the material from the vasculature, and wherein the negative pressure element and the chamber remain stationary during rotation of the proximal rotating element and the catheter.

According to an embodiment, the proximal rotating element may include a trigger configured to generate a linear motion; and an actuation system configured to translate the linear motion into a rotational motion, the rotational motion configured to rotate the catheter.

According to an embodiment, the trigger may include a lever, a high pivot point trigger, or a low pivot point trigger.

According to an embodiment, the actuation system may include a rack, a pinon gear, and a crown gear.

According to an embodiment, the actuation system may include a linkage, a half-moon gear, and a crown gear.

According to an embodiment, the actuation system may include a linkage, a cam, and a cam follower.

According to an embodiment, the actuation system may include a cable, a pulley, a spindle, and a return spring.

According to an embodiment, the actuation system may include a gear set, a helix, and a pair of shuttles.

According to an embodiment, the actuation system may include a gear set, a constant force spring, and a one-way locking bearing.

According to an embodiment, the actuation system is separated from a liquid flow path configured to contain the material being removed from the vasculature.

According to an embodiment, the device may include a rotational seal, the rotational seal configured to allow the negative pressure element to remain stationary during rotation of the proximal rotating element and the catheter.

According to an embodiment, the proximal rotating element may be configured to alternately rotate the catheter in a clockwise and counter-clockwise direction.

According to an embodiment, the proximal rotating element and the catheter may rotate in a first direction upon depression of a trigger and rotate in a second, opposite direction upon release of the trigger.

According to an embodiment, the negative pressure element may include a valve configured to control the suction in the chamber; and a locking plunger.

According to an embodiment, the negative pressure element may include a bellows; and a spring-biased piston.

According to an embodiment, the negative pressure element may include a suction barb.

According to an embodiment, the device may include a surface feature on an outer surface of the catheter, the surface feature configured to scrape an interior wall of the vasculature.

According to an embodiment, a method for removing material from a vasculature may include applying an external pressure cuff distal to a location for treatment; inserting a catheter into the vasculature and locating a distal tip of the catheter at the location for treatment; creating a suction within a chamber of a device; rotating the distal tip of the catheter; and suctioning material from the vasculature through a lumen of the catheter and into the chamber of the device, wherein rotating the distal tip of the catheter assists in removal of the material from the vasculature, and wherein the chamber remains stationary during rotation of the distal tip of the catheter.

According to an embodiment, applying the external pressure cuff distal to the location for treatment may create a dam within the vasculature preventing flow distally from the cuff.

According to an embodiment, creating the suction within the chamber of the device may include closing a valve and withdrawing a plunger from the chamber, thus creating a suction force within the chamber and then opening the valve to suction the material from the vasculature, through the lumen of the catheter, and into the chamber.

According to an embodiment, the device may allow for creation of a controlled suction.

According to an embodiment, rotating the distal tip of the catheter may include repeatedly depressing and releasing a trigger to cause continual rotation of the catheter.

According to an embodiment, rotating the distal tip of the catheter may alternate between rotation in a clockwise and counter-clockwise direction.

According to an embodiment, the method may include performing an interventional procedure in the vasculature, wherein the material is debris caused by the interventional procedure.

According to an embodiment, a device for removing material from a vasculature may include a catheter having a lumen, a proximal end, and a distal tip; an actuation system coupled to the proximal end of the catheter, the actuation system configured to rotate the catheter; and a locking syringe configured to create a controlled suction within a lumen of the device to remove the material from the vasculature, wherein the distal tip of the catheter rotates to assist in removal of the material from the vasculature, and wherein the locking syringe remains stationary during rotation of catheter.

According to an embodiment, the actuation system comprises a trigger, a helix gear, a gear/drive, a helix, a drive shuttle a free shuttle and a compression spring.

According to an embodiment, the device further comprising a slip ring, the slip ring configured to reduce friction between the compression spring and the drive shuttle.

According to an embodiment, the actuation system is configured to translate linear motion of a trigger into rotation motion of gears and the catheter.

According to an embodiment, a valve, the valve configured to allow flow from the lumen into the locking syringe and prevent flow from the locking syringe into the lumen.

Use of language such as "at least one of X, Y, and Z," "at least one of X, Y, or Z," "at least one or more of X, Y, and Z," "at least one or more of X, Y, or Z," "at least one or more of X, Y, and/or Z," or "at least one of X, Y, and/or Z," are intended to be inclusive of both a single item (just X, or just Y, or just Z) and multiple items (i.e., {X and Y}, {X and Z}, {Y and Z}, or {X, Y, and Z}). "At least one of" is not intended to convey a requirement that each possible item must be present.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A device for removing material from a vasculature, the device comprising: a rotation subassembly having a first central axis and a first gear, the rotation subassembly coupled to a catheter to rotate the catheter;

a valve subassembly having the first central axis and being adjacent to the rotation subassembly, the valve subassembly configured to selectively allow flow of the material from the catheter to the device; and an actuation system having a second central axis and a second gear, the actuation system configured to actuate rotation of the rotation subassembly, wherein the first central axis and the second central axis are parallel.

2. The device of claim 1, further comprising the catheter.

3. The device of claim 1, wherein the rotation subassembly comprises a body, the first gear, and a coupling configured to connect to the catheter.

4. The device of claim 3, wherein the body, the first gear, and the coupling are monolithic and unitary.

5. The device of claim 3, further comprising a protrusion extending within the coupling and forming an annular space with the body, wherein an end of the catheter is configured to be received within the annular space.

6. The device of claim 5, further comprising an internal threaded surface in the annular space, the internal threaded surface configured to correspond to a threaded surface on the end of the catheter.

7. The device of claim 1, wherein the first gear includes gear teeth and a protrusion having two lobes and the actuation system includes a helix having two protrusions, wherein the two protrusions are received within the two lobes to allow co-rotation between the helix and the first gear.

8. The device of claim 1, the actuation system further comprising a trigger, a free shuttle, and a drive shuttle.

9. The device of claim 8, wherein the free shuttle includes two protrusions configured to be received within respective openings of the trigger.

10. The device of claim 8, wherein the free shuttle and the drive shuttle are configured to move longitudinally along the second central axis.

11. The device of claim 8, wherein the drive shuttle is configured to rotate only in one direction about the second central axis.

12. The device of claim 8, wherein the free shuttle has a first ratchet profile and the drive shuttle has a second ratchet profile, the first ratchet profile configured to mate with the second ratchet profile.

13. The device of claim 12, wherein the mating of the first ratchet profile and the second ratchet profile allows rotation of the drive shuttle in a first direction and prevents rotation of the drive shuttle in a second direction.

14. The device of claim 12, wherein the first ratchet profile and the second ratchet profile each comprise a plurality of steps.

15. The device of claim 8, further comprising a helix.

16. The device of claim 15, wherein the helix has an external helix profile and the drive shuttle has an internal helix profile, wherein the internal helix profile is configured to mate with the external helix profile to allow relative rotation between the helix and the drive shuttle.

* * * * *